United States Patent
Shao et al.

(10) Patent No.: US 9,663,534 B2
(45) Date of Patent: May 30, 2017

(54) FUSED BICYCLIC ISOXAZOLINES AS INHIBITORS OF CHOLESTEROL ESTER TRANSFER PROTEIN

(71) Applicant: Merck Sharp & Dohme Corp., Rahway, NJ (US)

(72) Inventors: Pengcheng Patrick Shao, Fanwood, NJ (US); Feng Ye, Scotch Plains, NJ (US); Petr Vachal, Summit, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/104,351

(22) PCT Filed: Dec. 12, 2014

(86) PCT No.: PCT/US2014/069878
§ 371 (c)(1),
(2) Date: Jun. 14, 2016

(87) PCT Pub. No.: WO2015/094932
PCT Pub. Date: Jun. 25, 2015

(65) Prior Publication Data
US 2016/0318950 A1    Nov. 3, 2016

Related U.S. Application Data

(60) Provisional application No. 61/917,132, filed on Dec. 17, 2013.

(51) Int. Cl.
C07D 498/04    (2006.01)
C07D 231/54    (2006.01)
C07D 413/04    (2006.01)
C07D 413/10    (2006.01)
C07D 413/12    (2006.01)
A61K 31/423    (2006.01)
A61K 31/4439   (2006.01)
A61K 31/444    (2006.01)
A61K 45/06     (2006.01)
C07D 261/20    (2006.01)
C07D 413/14    (2006.01)

(52) U.S. Cl.
CPC .......... *C07D 498/04* (2013.01); *A61K 31/423* (2013.01); *A61K 31/444* (2013.01); *A61K 31/4439* (2013.01); *A61K 45/06* (2013.01); *C07D 231/54* (2013.01); *C07D 261/20* (2013.01); *C07D 413/04* (2013.01); *C07D 413/10* (2013.01); *C07D 413/12* (2013.01); *C07D 413/14* (2013.01)

(58) Field of Classification Search
CPC .................................................. C07D 498/04
See application file for complete search history.

(56) References Cited

U.S. PATENT DOCUMENTS

| | | |
|---|---|---|
| 7,652,049 B2 | 1/2010 | Ali et al. |
| 7,737,295 B2 | 6/2010 | Ali et al. |
| 7,781,426 B2 | 8/2010 | Ali et al. |
| 7,910,592 B2 | 3/2011 | Ali et al. |
| 7,915,271 B2 | 3/2011 | Ali et al. |
| 8,293,721 B2 | 10/2012 | Hunt et al. |
| 8,334,290 B2 | 12/2012 | Ali et al. |
| 8,436,028 B2 | 5/2013 | Hunt et al. |
| 8,445,480 B2 | 5/2013 | Hunt et al. |
| 8,486,983 B2 | 7/2013 | Sheth et al. |
| 8,865,707 B2 | 10/2014 | Ali et al. |
| 8,871,738 B2 | 10/2014 | Shao et al. |
| 9,126,976 B2 | 9/2015 | Anand et al. |
| 9,221,834 B2 | 12/2015 | Lu et al. |
| 9,353,101 B2 | 5/2016 | Acton, III et al. |
| 9,376,408 B2 | 6/2016 | Shao et al. |
| 2013/0040978 A1 | 2/2013 | Duffy et al. |
| 2013/0109649 A1 | 5/2013 | Shao et al. |
| 2015/0342931 A1 | 12/2015 | Ondeyka et al. |
| 2016/0185784 A1 | 6/2016 | Liu et al. |

FOREIGN PATENT DOCUMENTS

WO    WO2015094932 A1    6/2015

OTHER PUBLICATIONS

International Search Report and Written Opinion for PCT/US2014/069878 mailed Mar. 2, 2015; 7 pages.
PubChem. Compound Summary for CID 10422646, Retrieved from the Internet Feb. 9, 2015, URL: https://pubchem.ncbi.nlm.nih.gov/compound/10422646, Oct. 25, 2006.
PubChem. Compound Summary for CID 10611728, Retrieved from the Internet Feb. 9, 2015, URL: https://pubchem.ncbi.nlm.nih.gov/compound/10611728, Oct. 25, 2006.

*Primary Examiner* — Bruck Kifle
(74) *Attorney, Agent, or Firm* — Eric A. Meade; Catherine D. Fitch

(57) ABSTRACT

Compounds having the structure of Formula I, including pharmaceutically acceptable salts of the compounds, wherein X is ($CH_2$) or O, are CETP inhibitors and are useful for raising HDL-cholesterol, reducing LDL-cholesterol, and for treating or preventing atherosclerosis:

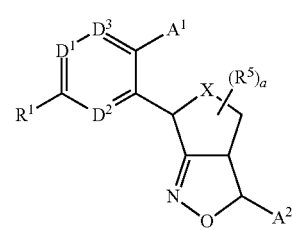

15 Claims, No Drawings

FUSED BICYCLIC ISOXAZOLINES AS INHIBITORS OF CHOLESTEROL ESTER TRANSFER PROTEIN

CROSS-REFERENCE TO RELATED APPLICATIONS

This application is a U.S. National Phase application under 35 U.S.C. §371 of PCT/US14/069878, filed Dec. 12, 2014, which claims priority from U.S. provisional application No. 61/917,132 filed Dec. 17, 2013.

FIELD OF THE INVENTION

This invention relates to chemical compounds that inhibit cholesterol ester transfer protein (CETP) and that are expected to have utility in raising HDL-C, lowering LDL-C, and in the treatment and prevention of atherosclerosis.

BACKGROUND OF THE INVENTION

Atherosclerosis and its clinical consequences, including coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA reductase inhibitors, especially the statins, in reducing coronary events is based on the reduction of circulating low density lipoprotein cholesterol (LDL-C), levels of which correlate directly with an increased risk for atherosclerosis. More recently, epidemiologic studies have demonstrated an inverse relationship between high density lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoprotein and transports cholesterol ester from HDL to the apoB lipoprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120(3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering LDL-C.

Despite the significant therapeutic advance that statins such as simvastatin and atorvastatin represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin provides an effective therapy for raising HDL-C but suffers from patient compliance issues, due in part to side effects such as flushing. Drugs that inhibit CETP (CETP inhibitors) have been under development with the expectation that they will effectively raise HDL cholesterol levels and also reduce the incidence of atherosclerosis in patients. Torcetrapib was the first drug that was tested in a long-term outcomes clinical trial. The clinical trial of torcetrapib was terminated early due to a higher incidence of mortality in patients to whom torcetrapib and atorvastatin were administered concomitantly compared with patients who were treated with atorvastatin alone. The cause of the increased mortality is not completely understood, but it is not believed to be associated with the CETP inhibiting effects of the drug. Dalcetrapib was recently tested in a Phase III outcomes trial, which was terminated early because the interim data did not show a clinical benefit. There were no safety issues detected for dalcetrapib.

Anacetrapib is currently the only CETP inhibitor being tested in a large scale Phase III clinical outcomes trial. Data from the recently completed DEFINE Phase II/III trial of anacetrapib are promising. Patients who were treated with anacetrapib along with baseline statin therapy showed an increase of HDL-C of 138% and a decrease of LDL-C of 40% compared with patients who were treated with just a statin. See: *N. Engl. J. Med.* 2010: 363: 2406-15. The DEFINE study was not carried out on a large enough scale to serve as a pivotal outcomes trial, but the data in the DEFINE trial were sufficient to indicate that an increase in mortality for patients treated with anacetrapib is unlikely. Additional drug candidates are in development. Evacetrapib currently appears to be the next CETP inhibitor that will proceed to a Phase III outcomes trial. Additional compounds are being sought that may have properties that are advantageous compared with the CETP inhibitors that have so far been studied or are currently being studied. Such properties may include, for example, higher potency, reduced off-target activity, better pharmacodynamics, higher bioavailability, or a reduced food effect compared with many of the highly lipophilic compounds that have so far been studied. "Food effect" refers to the variability in exposure to the active drug that occurs depending on when the patient had last eaten, whether or not the drug is administered with food, and the fat content of the food.

SUMMARY OF THE INVENTION

The compound of Formula I, or a pharmaceutically acceptable salt thereof, is a potent CETP inhibitor, having the utilities described below:

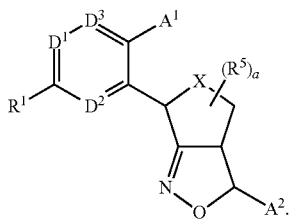

In the compound of Formula I:

X is —CH$_2$—, —O—, —C(=O)—, S, —S(O)—, —S(O)$_2$—, —C(=NR)—, or —NR—;

R is H, —CN, or —C$_1$-C$_5$ alkyl;

R$^1$ is H, —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, —OC$_2$-C$_5$ alkynyl, —OH, halogen, —CN, —NR$^6$R$^7$, —CO$_2$R$^8$, —C(O)NR$^6$R$^7$, —SO$_2$NR$^6$R$^7$, HET(3), or C$_{3-6}$ cycloalkyl optionally having 1-2 double bonds, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, and —OC$_2$-C$_5$ alkynyl are each optionally substituted with 1-7 halogens, and wherein HET(3) and C$_{3-6}$ cycloalkyl optionally having 1-2 double bonds are optionally substituted with 1-3 substituent groups which are each independently halogen, —C$_1$-C$_3$ alkyl, —OC$_1$-C$_3$ alkyl, —C$_2$-C$_3$ alkenyl, —OC$_2$-C$_3$ alkenyl, —C$_2$-C$_3$ alkynyl, or —OC$_2$-C$_3$ alkynyl, wherein —C$_1$-C$_3$ alkyl, —OC$_1$-C$_3$ alkyl, —C$_2$-C$_3$ alkenyl, —OC$_2$-C$_3$ alkenyl, —C$_2$-C$_3$alkynyl, and —OC$_2$-C$_3$ alkynyl are each optionally substituted with 1-7 halogens;

R$^6$ and R$^7$ are each independently H, —C$_1$-C$_5$ alkyl, phenyl, naphthyl, C$_{3-6}$ cycloalkyl optionally having 1-2 double bonds, or HET(3), wherein when R$^6$ and R$^7$ are each alkyl, R$^6$ and R$^7$ are optionally joined to form a 4-7 membered cyclic amine group which is optionally substituted with 1-2 groups independently selected from halogen, CH$_3$, CF$_3$, OCH$_3$, or OCF$_3$, wherein phenyl, naphthyl, C$_{3-6}$ cycloalkyl, and HET(3) are optionally substituted with 1-3 substituent groups which are each independently halogen, —C$_1$-C$_3$ alkyl, —OC$_1$-C$_3$ alkyl, —C$_2$-C$_3$ alkenyl, —OC$_2$-C$_3$ alkenyl, —C$_2$-C$_3$ alkynyl, or —OC$_2$-C$_3$ alkynyl, wherein —C$_1$-C$_3$ alkyl, —OC$_1$-C$_3$ alkyl, —C$_2$-C$_3$ alkenyl, —OC$_2$-C$_3$ alkenyl, —C$_2$-C$_3$alkynyl, and —OC$_2$-C$_3$ alkynyl are each optionally substituted with 1-7 halogens;

R$^8$ is H or —C$_{1-5}$alkyl optionally substituted with 1-7 halogens;

HET(3) is a 3-6 membered heterocyclic ring having 1-3 heteroatom groups which are each independently N, NH, O, S, S(O), or S(O)$_2$ and optionally having 1-3 double bonds;

D$^1$ is N or CR$^2$;
D$^2$ is N or CR$^3$;
D$^3$ is N or CR$^4$;

R$^2$, R$^3$, and R$^4$ are each independently H, —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, —OC$_2$-C$_5$ alkynyl, —OH, halogen, —CN, —NR$^6$R$^7$, —CO$_2$R$^8$, —C(O)NR$^6$R$^7$, or —SO$_2$NR$^6$R$^7$, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, and —OC$_2$-C$_5$ alkynyl are optionally substituted with 1-7 halogens;

Each R$^5$ is independently —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, —OC$_2$-C$_5$ alkynyl, —OH, halogen, —CN, —NR$^6$R$^7$, —CO$_2$R$^8$, —C(O)NR$^6$R$^7$, or —SO$_2$NR$^6$R$^7$, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, and —OC$_2$-C$_5$ alkynyl are optionally substituted with 1-7 halogens;

A$^1$ is phenyl, HET(1), or C$_3$-C$_8$ cycloalkyl optionally having 1-2 double bonds, wherein A$^1$ is optionally substituted with one substituent group Z and is optionally substituted with 1-3 groups which are each independently —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, —OC$_2$-C$_5$ alkynyl, halogen, —OH, or —CN, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, and —OC$_2$-C$_5$ alkynyl are optionally substituted with 1-7 halogens;

HET(1) is a 5- or 6-membered heterocyclic ring having 1-4 heteroatom groups which are each independently —N—, —NH—, —S—, —O—, —S(O)—, or —S(O)$_2$—, optionally having one group —C(=O)—, and optionally having 1-3 double bonds;

Z is A$^3$, —C$_1$-C$_3$ alkylene-CO$_2$R$^8$, —C$_1$-C$_3$ alkylene-C(O)NR$^6$R$^7$, —C$_1$-C$_3$ alkylene-SO$_2$NR$^6$R$^7$, —CO$_2$R$^8$, —C(O)NR$^6$R$^7$, —SO$_2$NR$^6$R$^7$, or —C$_1$-C$_3$alkylene-HET(2), wherein —C$_1$-C$_3$alkylene in all uses is optionally substituted with 1-6 halogens, 1-2 CH$_3$, and 1 —OH, and HET(2) is optionally substituted with 1-3 substituents which are independently —C$_{1-3}$alkyl optionally substituted with 1-5 halogens, —OC$_{1-3}$alkyl optionally substituted with 1-5 halogens, halogen or NR$_6$R$_7$;

A$^3$ is phenyl, C$_3$-C$_6$ cycloalkyl optionally having 1-2 double bonds, or HET(1), wherein A$^3$ is optionally substituted with 1-3 groups which are each independently —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, —OC$_2$-C$_5$ alkynyl, halogen, —OH, or —CN, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, and —OC$_2$-C$_5$ alkynyl are optionally substituted with 1-7 halogens; and A$^3$ is optionally substituted with one group which is HET(2), —C$_{1-4}$ alkylene-CO$_2$R$^8$, —C$_{1-4}$alkylene-C(O)NR$^6$R$^7$, —C$_1$-C$_4$alkylene-SO$_2$NR$^6$R$^7$, —CO$_2$R$^8$, —C(O)NR$^6$R$^7$, —SO$_2$NR$^6$R$^7$, or —C(O)NR$^6$C$_{3-6}$cycloalkyl in which C$_{3-6}$cycloalkyl is optionally substituted with 1-3 substituents which are independently selected from halogen, C$_{1-2}$alkyl, and —CN, wherein —C$_1$-C$_4$alkylene in all uses is optionally substituted with 1-7 halogens; and wherein HET(2) is optionally substituted with 1-3 groups which are each independently halogen, —C$_{1-5}$alkyl optionally substituted with 1-7 halogens, —OC$_{1-5}$alkyl optionally substituted with 1-7 halogens, or NR$^6$R$^7$;

HET(2) is a 5-6 membered heterocyclic ring having 1-3 heteroatom groups which are each independently N, NH, O, or S, optionally having one group —C(=O)—, and optionally having 1-3 double bonds;

A$^2$ is phenyl or HET(1), wherein A$^2$ is optionally substituted with 1-3 substituent groups which are each independently —C$_1$-C$_5$ alkyl, —OC$_1$-C$_5$ alkyl, —C$_2$-C$_5$ alkenyl, —OC$_2$-C$_5$ alkenyl, —C$_2$-C$_5$alkynyl, —OC$_2$-C$_5$alkynyl, halogen, —CN, —OH, or C$_{3-6}$cycloalkyl, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$alkynyl, and —OC$_2$-C$_5$ alkynyl are optionally substituted with 1-7 halogens, and C$_{3-6}$cycloalkyl is optionally substituted with 1-3 substituents which are each independently halogen, —C$_1$-C$_3$ alkyl, or —OC$_1$-C$_3$ alkyl, wherein —C$_1$-C$_3$ alkyl and —OC$_1$-C$_3$ alkyl are each optionally substituted with 1-7 halogens; and a is 0 or an integer from 1-6.

In the compound(s) of Formula I, and in subgroups and other embodiments of the invention, alkyl groups and substituents based on alkyl groups, such as alkoxy, may be linear or branched unless otherwise indicated.

In general, references to the compound(s) of formula I are meant to also include subsets of compounds of formula I as may be defined herein, and also are meant to include the specific numbered examples provided herein. In further embodiments of the invention that are defined herein, the defined substituent groups may have alternative values independent of one another and can be varied in different embodiments independently of one another. Such embodiments include pharmaceutically acceptable salts when such salts are possible.

DETAILED DESCRIPTION OF THE INVENTION

In many embodiments, $R^1$ is $—C_1-C_5$ alkyl, $—OC_1-C_5$ alkyl, halogen, $—NR^6R^7$, HET(3), or $C_{3-6}$ cycloalkyl optionally having 1-2 double bonds, wherein $—C_1-C_5$ alkyl and $—OC_1-C_5$ alkyl are optionally substituted with 1-7 halogens, and wherein HET(3) and $C_{3-6}$ cycloalkyl optionally having 1-2 double bonds are optionally substituted with 1-3 substituent groups which are each independently halogen, $CH_3$, $CF_3$, $OCH_3$, or $OCF_3$.

In many embodiments, at least one of $D^1$, $D^2$, and $D^3$ is $CR^2$, $CR^3$, or $CR^4$.

In many embodiments, $R^2$, $R^3$, and $R^4$ are each independently H, $—C_1-C_5$ alkyl, $—OC_1-C_5$ alkyl, or halogen, wherein $—C_1-C_5$ alkyl and $—OC_1-C_5$ alkyl are optionally substituted with 1-7 halogens.

In many embodiments, each $R^5$ is independently $—C_1-C_5$ alkyl, $—OC_1-C_5$ alkyl, or halogen, wherein $—C_1-C_5$ alkyl and $—OC_1-C_5$ alkyl are optionally substituted with 1-7 halogens.

In many embodiments, $A^1$ is phenyl, HET(1), or $C_3-C_6$ cycloalkyl optionally having 1-2 double bonds, wherein $A^1$ is optionally substituted with one substituent group Z and is optionally substituted with 1-3 groups which are each independently halogen, $—OH$, $—CN$, $—C_{1-5}$alkyl optionally substituted with 1-7 halogens, or $—OC_{1-5}$alkyl optionally substituted with 1-7 halogens.

In many embodiments, $A^1$ has at least one substituent group.

In many embodiments, $A^3$ is phenyl, $C_3-C_6$ cycloalkyl optionally having 1-2 double bonds, or HET(1), wherein $A^3$ is optionally substituted with 1-3 groups which are each independently $—C_1-C_5$ alkyl optionally substituted with 1-7 halogens, $—OC_1-C_5$ alkyl optionally substituted with 1-7 halogens, $—OH$, or halogen, and is optionally substituted with one group which is HET(2), $—C_{1-2}$ alkylene-$CO_2R^8$, $—C_{1-2}$alkylene-$C(O)NR^6R^7$, $—C_1-C_2$alkylene-$SO_2NR^6R^7$, $—CO_2R^8$, $—C(O)NR^6R^7$, $—SO_2NR^6R^7$, or $—C(O)NR^6 C_{3-6}$cycloalkyl wherein $C_{3-6}$cycloalkyl is optionally substituted with 1-3 substituents which are independently selected from halogen, $C_{1-2}$alkyl, and $—CN$, wherein $—C_1-C_2$alkylene is optionally substituted with 1-3 halogens; and wherein HET(2) is optionally substituted with 1-3 groups which are each independently halogen, $—C_{1-5}$alkyl optionally substituted with 1-7 halogens, $—OC_{1-5}$alkyl optionally substituted with 1-7 halogens, or $NR^6R^7$.

In many embodiments, $A^2$ is phenyl or HET(1), wherein $A^2$ is optionally substituted with 1-3 substituent groups which are each independently $C_{1-5}$alkyl optionally substituted with 1-7 halogens, $—OC_{1-5}$alkyl optionally substituted with 1-7 halogens, halogen, $—OH$, $—CN$, or $C_{3-6}$cycloalkyl optionally substituted with 1-3 substituents which are each independently halogen, $CF_3$, $CH_3$, $—OCF_3$, or $—OCH_3$.

In many embodiments, a is 0 or an integer from 1-3.

In many many embodiments, X is $—CH_2—$ or $—O—$.

In many embodiments, $R^1$ is $CH_3$, $CF_3$, $—OCH_3$, $—OCF_3$, halogen, or $—NR^6R^7$.

In many embodiments, $R^6$ and $R^7$ are each independently H or $—C_1-C_5$ alkyl.

In many embodiments, $R^2$, $R^3$, and $R^4$ are each independently H, $C_{1-3}$alkyl, $CF_3$, $—OC_{1-3}$alkyl, $—OCF_3$, or halogen.

In many embodiments, each $R^5$ is independently $CH_3$, $CF_3$, $—OCH_3$, $—OCF_3$, or halogen.

In many embodiments, $A^1$ is phenyl, HET(1), or $C_3-C_6$ cycloalkyl optionally having 1-2 double bonds, wherein $A^1$ is optionally substituted with one substituent group Z and is optionally substituted with 1-3 groups which are each independently $—C_{1-3}$alkyl optionally substituted with 1-5 halogens, $—OC_{1-3}$alkyl optionally substituted with 1-5 halogens, halogen, $—OH$, or $—CN$.

In many embodiments, each HET(1) is a 5- or 6-membered heterocyclic ring having 1-3 heteroatom groups which are each independently $—N—$, $—NH—$, $—S—$, or $—O—$, optionally having one group $—C(=O)—$, and optionally having 1-3 double bonds.

In many embodiments, Z is $A^3$, $—(CH_2)_{1-3}—CO_2R^8$, $—(CH_2)_{1-3}—C(O)NR^6R^7$, $—(CH_2)_{1-3}—SO_2NR^6R^7$, $—CO_2R^8$, $—C(O)NR^6R^7$, $—SO_2NR^6R^7$, or $—(CH_2)_{1-3}$-HET(2), wherein HET(2) is optionally substituted with 1-3 substituents which are independently $—C_{1-3}$alkyl optionally substituted with 1-5 halogens, $—OC_{1-3}$alkyl optionally substituted with 1-5 halogens, halogen or $NR_6R_7$.

In many embodiments, $R^8$ is H or $—C_{1-3}$alkyl optionally substituted with 1-3 halogens.

In many embodiments, $A^3$ is phenyl, $C_3-C_6$ cycloalkyl optionally having 1-2 double bonds, or HET(1), wherein $A^3$ is optionally substituted with 1-3 groups which are each independently $CH_3$, $CF_3$, $—OCH_3$, $—OCF_3$, $—OH$, or halogen, and is optionally substituted with one group which is HET(2), $—(CH_2)_{1-2}—CO_2R^8$, $—(CH_2)_{1-2}—C(O)NR^6R^7$, $—(CH_2)_{1-2}—SO_2NR^6R^7$, $—CO_2R^8$, $—C(O)NR^6R^7$, $—SO_2NR^6R^7$, or $—C(O)NR^6$cyclopropyl, wherein cyclopropyl is optionally substituted with 1-3 substituents which are independently selected from 1-3 halogens, one $CH_3$, and one $—CN$, and HET(2) is optionally substituted with 1-3 groups which are each independently $CH_3$, $CF_3$, $—OCH_3$, $—OCF_3$, halogen, or $NR^6R^7$.

In many embodiments, $A^2$ is phenyl or HET(1), wherein $A^2$ is substituted with 1-3 substituent groups which are each independently $CH_3$, $CF_3$, $—OCH_3$, $—OCF_3$, halogen, $—CN$, $—OH$, or $C_{3-4}$cycloalkyl optionally substituted with 1-3 substituents which are each independently halogen, $CF_3$, $CH_3$, $—OCF_3$, or $—OCH_3$.

In many embodiments, a is 0, 1, or 2.

In many embodiments, $R^1$ is $CH_3$, $CF_3$, $—OCH_3$, $—OCF_3$, F, Cl, or $—NR^6R^7$.

In many embodiments, $R^6$ and $R^7$ are each independently H or $—C_1-C_3$ alkyl.

In many embodiments, $D^1$ is N or $CR^2$, wherein $R^2$ is H, $—C_{1-3}$alkyl, F, or Cl.

In many embodiments, $D^2$ is N or $CR^3$, wherein $R^3$ is H, $—C_{1-3}$alkyl, F, or Cl.

In many embodiments, $D^3$ is N or $CR^4$, wherein $R^4$ is H, $—C_{1-3}$alkyl, F, or Cl.

In many embodiments, at least one of $D^1$, $D^2$, or $D^3$ is $CR^2$, $CR^3$, or $CR^4$.

In many embodiments, $R^5$ is H or $CH_3$.

In many embodiments, $A^1$ is phenyl, pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, cyclopropyl, cyclobutyl, cyclohexyl, cyclohexenyl, cyclopentyl, or cyclopentenyl, wherein $A^1$ is optionally substituted with 1-3 groups which are each independently F, Cl, —OCH$_3$, —OCF$_3$, —C$_{1-3}$alkyl, —CN, or CF$_3$, and optionally one substituent group Z.

In many embodiments, Z is $A^3$, —CH$_2$CH$_2$CO$_2$R$^8$, —CH$_2$CH$_2$C(O)NR$^6$R$^7$, —CH$_2$CH$_2$SO$_2$NR$^6$R$^7$, or —CH$_2$CH$_2$-HET(2), wherein HET(2) is optionally substituted with 1-2 substituent groups which are each independently CH$_3$, CF$_3$, —OCH$_3$, —OCF$_3$, halogen, or NR$^6$R$^7$.

In many embodiments, R$^8$ is H or —CH$_3$.

In many embodiments, HET(2) is a 5-membered heterocyclic ring having 1-3 heteroatom groups which are each independently N, NH, O, or S, optionally having one group —C(=O), and optionally having 1-3 double bonds.

In many embodiments, $A^3$ is phenyl, cyclopropyl, cyclobutyl, cyclohexyl, cyclohexenyl, cyclopentyl, cyclopentenyl, or HET(1), wherein HET(1) is pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, or a 5-6-membered heterocyclic ring having 1-2 heteroatom groups which are independently —N—, —NH— or —O—, and optionally one —C(=O)— group, wherein $A^3$ is optionally substituted with 1-2 groups which are each independently CH$_3$, CF$_3$, —OCH$_3$, —OCF$_3$, —OH, or halogen, and is optionally substituted with 1 group which is —CO$_2$R$^8$, —C(O)NR$^6$R$^7$, —SO$_2$NR$^6$R$^7$, HET(2), or —C(O)NR$^6$cyclopropyl wherein cyclopropyl is optionally substituted with 1-3 substituents which are independently selected from 1-3 halogens, one CH$_3$ and one —CN, and HET(2) is optionally substituted with 1-2 substituent groups which are each independently CH$_3$, CF$_3$, —OCH$_3$, —OCF$_3$, halogen, or NR$^6$R$^7$.

In many embodiments, $A^2$ is phenyl or HET(1) wherein $A^2$ is optionally substituted with 1-3 substituent groups which are each independently CF$_3$, CH$_3$, F, Cl, —CN, or cyclopropyl.

In many embodiments, a is 0 or 1.

In many embodiments, a is 0.

In many embodiments, the compounds can be defined using figure I or Ia with the substituent definitions as written above or as written hereafter.

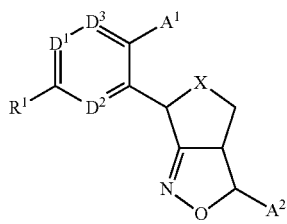

Ia

In many embodiments, X is —CH$_2$— or —O—.

In many embodiments, R$^1$ is CF$_3$, F, or —N(CH$_3$)$_2$.

In many embodiments, R$^6$ and R$^7$ are each independently H or —CH$_3$.

In many embodiments, D$^1$ is N or CR$^2$, wherein R$^2$ is H or C$_{1-3}$alkyl.

In many embodiments, D$^2$ is N or CR$^3$, wherein R$^3$ is H or CH$_3$.

In many embodiments, D$^3$ is N or CR$^4$, wherein R$^4$ is H or CH$_3$.

In many embodiments, $A^1$ is phenyl, pyridinyl, thienyl, furyl, cyclohexenyl, or cyclopentenyl, wherein $A^1$ is optionally substituted with 1-3 groups which are each independently F, Cl, —OCH$_3$, isopropyl, —CN, —CH$_3$, or CF$_3$, and optionally one substituent group Z.

In many embodiments, Z is $A^3$, —CH$_2$CH$_2$CO$_2$R$^8$, —CH$_2$CH$_2$-(5-oxo-4,5-dihydro-1,3,4-oxadiazol-2-yl), or —CH$_2$CH$_2$-(5-amino-1,3,4-oxadiazol-2-yl).

In many embodiments, R$^8$ is H or —CH$_3$.

In many embodiments, $A^3$ is phenyl, cyclobutyl, cyclopentyl, cyclohexyl, or HET(1), wherein HET(1) is pyridinyl, 6-oxopiperidinyl, 2-oxo-1,3-oxazolidinyl, 2-oxo-1,3-oxazinanyl, 5-oxopyrrolidinyl, -(5-oxo-4,5-dihydro-1,3,4-oxadiazol-2-yl), or -(5-amino-1,3,4-oxadiazol-2-yl) wherein $A^3$ is optionally substituted with 1-2 groups —CH$_3$, —OCH$_3$, or —OH, and is optionally substituted with 1 group which is —CO$_2$R$^8$ or —C(=O)NHcyclopropyl which is optionally substituted with 1-3 groups independently selected from one —CN and 1-3 halogens.

In many embodiments, $A^2$ is phenyl or pyridinyl, wherein $A^2$ is optionally substituted with 1 or 2 groups which are each independently CF$_3$, CH$_3$, F, or Cl.

In many embodiments, R$^1$ is CF$_3$.

In many embodiments, D$^1$ is N or CR$^2$, wherein R$^2$ is H.

In many embodiments, D$^2$ is N or CR$^3$, wherein R$^3$ is H.

In many embodiments, D$^3$ is CR$^4$, wherein R$^4$ is H.

In many embodiments, $A^1$ is phenyl or pyridinyl, wherein $A^1$ is optionally substituted with 1-3 groups which are each independently F, —OCH$_3$, or isopropyl, and optionally one substituent group Z.

In many embodiments, Z is $A^3$ or —CH$_2$CH$_2$CO$_2$R$^8$.

In many embodiments, R$^8$ is H or —CH$_3$.

In many embodiments, $A^3$ is phenyl or cyclohexyl, wherein $A^3$ is optionally substituted with 1-2 groups —CH$_3$ and is optionally substituted with 1 group —CO$_2$R$^8$.

In many embodiments, $A^2$ is phenyl or pyridinyl, wherein $A^2$ is optionally substituted with 1-2 groups which are selected from CF$_3$ and F.

In many embodiments, X is —CH$_2$—.

In many embodiments, X is —O—.

Definitions and Abbreviations

Many abbreviations are used in this application that are commonly used in chemistry. The list below provides most or all of these abbreviations. Abbreviations that are not listed below can normally be found in an internet search using Google or other search engines.

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, n-butyl, sec-butyl, tert-butyl, pentyl, hexyl, heptyl, octyl, nonyl, and the like.

"Alkylene" groups are alkyl groups that are difunctional rather than monofunctional. For example, methyl is an alkyl group and methylene (—CH$_2$—) is the corresponding alkylene group. Alkyl groups that are shown as difunctional are alkylene groups, even if they are referred to as alkyl groups.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" when used to describe a substituent or group in a structure means a monocyclic or bicyclic compound in which the rings are aromatic and which contain only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocycle" or "heterocyclic" means a fully or partially saturated cyclic compound containing 1 or more heteroatom groups which may be one or more of N, S, O, S(O), S(O)$_2$, or (N)R, and may have one or more double bonds, where R is H or a substituent group. In general, when heterocycles are defined herein, the definition will include the number of ring members, the number of double bonds (if any), and the specific heteroatoms. The heterocycles in some cases will be aromatic, depending on the number of double bonds (e.g. 6-membered ring with 3 double bonds). Aromatic heterocycles are also referred to as heteroaromatics or heteroaryls. S(O), S(O)$_2$, and N(R) are referred to as heteroatom groups, and each heteroatom group is counted as one ring member, as is also the case for N, S, and O.

"Benzoheterocycle" represents a phenyl ring fused to a heterocyclic ring. Examples include indole, benzofuran, 2,3-dihydrobenzofuran and quinoline.

"acac" is an abbreviation for acetylacetonate.
"AcN" is acetonitrile.
"Boc" is tert-butoxycarbonyl.
"n-BuLi" is n-butyl lithium.
"CDI" is 1,1'-carbonyldiimidazole.
"Celite®", "Celite" and "celite" all represent a brand of diatomaceous earth.
"DBU" is 1,8-diazabicyclo[5.4.0]undec-7-ene.
"D-Epoxone" is a commercial epoxidation catalyst.
"DIPEA" and "DIEA" are N,N-diisopropylethylamine.
"DCM" is dichloromethane.
"DIBAL-H" and "DIBAL" both represent diisobutylaluminum hydride.
"DIEA" is diisopropylethylamine.
"DMF" is N,N-dimethylformamide.
"DMA" is dimethylacetamide.
"DMAP" is 4-dimethylaminopyridine.
"DMSO" is dimethyl sulfoxide.
"DOPC" is 1,2-dioleoyl-sn-glycero-3-phosphocholine.
"EDTA" is ethylenediaminetetraacetic acid.
"EtOAc" is ethyl acetate.
"EtOH" is ethanol.
"Halogen" includes fluorine, chlorine, bromine and iodine.
"HPLC" is high pressure liquid chromatography.
"IPA" is isopropyl alcohol.
"LCMS" is liquid chromatography mass spectrometry.
"LiHMDS" is lithium hexamethyldisilazide.
"Lindlar catalyst" is a heterogeneous palladium hydrogenation catalyst that has been "poisoned" with lead to improve its selectivity.
"Me" represents methyl.
"MeCN" is acetonitrile.
"MeOH" is methanol.
"NCS" is N-chlorosuccinamide.
"NMP" is N-methyl-2-pyrrolidone.
"OAc" is acetate.
"OXONE®" is a commercial persulfate oxidizing agent from DuPont.
"Pd$_2$dba$_3$," is Tris(dibenzylideneacetone)dipalladium(0), a catalyst precursor.
"PEG" is poly(ethylene glycol).
"RBF" is a round bottom flask.
"Rochelle's salt" is potassium sodium tartrate.
"RT" is an abbreviation for room temperature.
"RuPhos" is Chloro-(2-Dicyclohexylphosphino-2',6'-diisopropoxy-1,1'-biphenyl)[2-(2-aminoethyl)phenyl]palladium(II), a commercial catalyst precursor.
"SFC" is supercritical fluid chromatography.
"SM" is starting material.
"Sonogashira coupling" is the name of a chemical reaction for coupling a terminal alkyne with an aryl halide.
"SPhos" is 2-Dicyclohexylphosphino-2',6'-dimethoxybiphenyl, a ligand.
"T3P®" is a trade name for a coupling reagent for amines and carboxylic acids to make an amide.
"TEA" is triethylamine.
"TFA" is trifluoroacetic acid.
"Tf$_2$O" is an abbreviation for trifluoromethanesulfonic anhydride.
"THF" is tetrahydrofuran.
"TLC" is thin layer chromatography.
"Xantphos" is (9,9-Dimethyl-9H-xanthene-4,5-diyl)bis (diphenylphosphine), a ligand.
"Xphos" is a name for a phosphine ligand that is used in selective coupling reactions.

The term "composition," as in pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I and a pharmaceutically acceptable carrier.

The substituent "tetrazole" means a 2H-tetrazol-5-yl substituent group and tautomers thereof.

Optical Isomers-Diastereomers-Geometric Isomers-Tautomers

The compounds disclosed herein generally have at least two asymmetric centers, and can thus occur as pure stereoisomers and as mixtures of stereoisomers, including racemates, racemic mixtures, single enantiomers, mixtures of enantiomers, diastereomeric mixtures and individual diastereomers. Different stereoisomers having the same 2-dimensional chemical structure may have different levels of activity with respect to CETP inhibition, so that some stereoisomers may have higher activity than others. The compounds that are potent inhibitors of CETP may have utility in patients for raising HDL-C, lowering LDL-C, treating dyslipidemia, and for preventing, treating or delaying the onset of conditions that are related to atherosclerosis. Stereoisomers that have little or no activity may have utility as research tools for better understanding CETP inhibition. All stereoisomers of the claimed compounds thus have utility. The compounds of Formula I may also occur as atropisomers (rotamers) due to hindered rotation, which may be observable by NMR spectroscopy, and in some cases may be stable enough with respect to conversion by bond rotation to other atropisomers that they can be isolated and assayed.

Salts

The term "pharmaceutically acceptable salts" refers to salts prepared from pharmaceutically acceptable non-toxic bases or acids including inorganic or organic bases and inorganic or organic acids. When the compound of Formula I is acidic, salts may be derived from inorganic bases including aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, triethanolamine, trimethylamine, tripropylamine, tromethamine, and the like.

When the compound of Formula I is basic, salts may be prepared from pharmaceutically acceptable non-toxic acids, including inorganic and organic acids. Such acids include acetic, adipic, ascorbic, benzenesulfonic, benzoic, camphorsulfonic, citric, diethylacetic, ethanesulfonic, formic, fumaric, gluconic, glutamic, hydrobromic, hydrochloric, isethionic, isonicotinic, lactic, maleic, malic, malonic, mandelic, methanesulfonic, mucic, naphthalenedisulfonic, nitric, oxalic, pamoic, pantothenic, phenylpropionic, phosphoric, pimelic, pivalic, propionic, salicylic, succinic, sulfuric, sulfaminic, tartaric, p-toluenesulfonic acid, trifluoroacetic and the like. Particularly preferred are citric, hydrobromic, hydrochloric, maleic, phosphoric, sulfuric, and tartaric acids.

It will be understood that, as used herein, references to the compounds of Formula I and to the examples are meant to also include the pharmaceutically acceptable salts and prodrugs, where such salts and prodrugs are possible.

Prodrugs

Prodrugs, which are compounds that are converted to the compound of Formula I as they are being administered to a patient or after they have been administered to a patient, are also compounds of formula I in the sense that they provide the claimed pharmaceutically active drug moiety to the patient.

Isotopes

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

The compounds disclosed herein, including pharmaceutically acceptable salts thereof, are potent inhibitors of CETP. The compounds may therefore be useful in treating mammalian patients, preferably human patients, having diseases and conditions that are treated by inhibition of CETP.

One aspect of the present invention provides a method for treating or reducing the risk of developing a disease or condition that may be treated or prevented by inhibition of CETP by administering a therapeutically effective amount of the compound of Formula I to a patient in need of treatment. The patient is a human or mammal, but is most often a human. A "therapeutically effective amount" is the amount of compound that is effective in obtaining a desired clinical outcome in the treatment of a specific disease or condition.

Diseases or conditions that may be treated with the compounds of Formula I, or which the patient may have a reduced risk of developing as a result of being treated with the compounds of Formula I, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome. There are reports in the scientific literature that suggest that inhibition of CETP may have utility in preventing or slowing the development of Alzheimer's disease. The compounds of Formula I may therefore have utility in preventing or delaying the progression of Alzheimer's disease or other neurodegenerative diseases.

The compounds disclosed herein are particularly effective in raising HDL-C and/or increasing the ratio of HDL-C to LDL-C. The compounds may also be effective in reducing LDL-C, and may be effective in treating dyslipidemia. These changes in HDL-C and LDL-C may be beneficial in treating atherosclerosis, reducing or delaying the development of atherosclerosis, reducing the risk of developing atherosclerosis, or preventing atherosclerosis. The compounds disclosed herein may thus be beneficial in treating atherosclerosis, reducing or delaying the development of atherosclerosis, reducing the risk of developing atherosclerosis, or preventing atherosclerosis.

Likely indications for atherosclerosis and dyslipidemia using the compounds described herein are written below, where the drug product is titled "CETP inhibitor:"

Atherosclerosis.

In patients at high risk of cardiovascular events because of existing coronary, cerebrovascular, or peripheral vascular disease, CETP inhibitor co-administered with an HMG-CoA reductase inhibitor is indicated to reduce the risk of coronary mortality, myocardial infarction, coronary revascularization procedures, ischemic stroke, and cardiovascular death.

Dyslipidemia.

CETP inhibitor co-administered with a statin is indicated to reduce elevated LDL-C, apolipoprotein B (ApoB), lipoprotein a (Lp(a)), non-HDL-C, and total cholesterol; and increase HDL-C and apolipoprotein A-1 (Apo A-1) in patients with mixed or primary dyslipidemia.

Administration and Dose Ranges

Any suitable route of administration may be employed for providing a mammal, especially a human, with an effective dose of the compounds described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably the compound of Formula I is administered orally.

When treating the diseases for which the compound of Formula I is indicated, generally satisfactory results are expected when the compound of Formula I is administered at a daily dosage of from about 0.1 milligram to about 1000 milligram in one dose daily or divided into more than one dose per day.

Oral administration will usually be carried out using tablets. Examples of doses in tablets include 0.1 mg, 0.5 mg, 1 mg, 2 mg, 5 mg, 10 mg, 25 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 275 mg, 300 mg, 350 mg, 400 mg, 450 mg, 500 mg, and 1000 mg. Other oral forms can also have the same dosages (e.g. capsules). A preferred dose is likely in the range of 50-200 mg.

Pharmaceutical Compositions

Another aspect of the present invention provides pharmaceutical compositions which comprise the compound of Formula I and a pharmaceutically acceptable carrier. The pharmaceutical compositions of the present invention comprise the compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. A pharmaceutical composition may also consist essentially of the compound of Formula I, or a pharmaceutically acceptable salt of the compound, and a pharmaceutically acceptable carrier, without other therapeutic ingredients.

Pharmaceutical compositions may be formulated to be suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compound of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compound can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compound of formula I may also be administered parenterally. Solutions or suspensions of the compound can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compound of Formula I, including pharmaceutically acceptable salts thereof, may be used in pharmaceutical combinations with other drugs that may also be useful in the treatment or amelioration of the diseases or conditions for which the compound of Formula I is useful. Such other drugs may be administered, by a route and in an amount commonly used therefore, contemporaneously or sequentially with the compound of Formula I. When the compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered concomitantly, on the same or different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of formula I and the other active ingredients may be used in lower doses than when each is used singly. Accordingly, the pharmaceutical compositions of the compound of formula I include those that contain one or more other active ingredients, in addition to the compound of Formula I.

The compound of Formula I will likely be approved initially for coadministration with a statin, which could be administered in the form of a fixed dose combination of the compound of formula I and a statin. Additional drugs may also be administered in combination with the compound of Formula I and the statin, either by coadministration or in a fixed dose combination. The compound of formula I and the drugs that are administered with it may be administered as pharmaceutically acceptable salts, as prodrugs, or otherwise formulated for immediate release, extended release, or controlled release, as necessary.

Examples of statins that may be administered in combination with the compound of Formula I include, but are not limited to, (i) simvastatin and lovastatin which are marketed as ZOCOR® and MEVACOR® in lactone prodrug form and function as inhibitors after administration, and (ii) dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), and pitavastatin (particularly the calcium salt sold in LIVALO®), and (iii) other statins that may yet be developed. Preferred statins for combination therapy include atorvastatin, rosuvastatin, and simvasatin, as described above.

Cholesterol absorption inhibitors, and particularly ezetimibe (ZETIA®), as well as other cholesterol absorption inhibitors, such as stanol esters, beta-sitosterol, sterol glycosides such as tiqueside, and other azetidinones, may be administered with the compound of Formula I, generally with a statin, as described above. The preferred cholesterol absorption inhibitor is ezetimibe. Combinations of the compound of formula I with a statin and a cholesterol inhibitor, such as ezetimibe, are also contemplated. Preferred 3-component combinations include combinations of the compound of formula I with simvastatin, atorvastatin, or rosuvastatin in combination with ezetimibe, where the statins may be salt forms or prodrugs as described above. The combination of simvastatin with ezetimibe is currently marketed as VYTORIN®.

Other cholesterol reducing drugs that may be coadministered with the compound of formula I in addition to HMG-CoA reductase inhibitors (statins) and cholesterol absorption inhibitors include (i) bile acid sequestrants, as for example cholestyramine, colestipol, dialkylaminoalkyl derivatives of a cross-linked dextran, Colestid®, and LoCholest®, (ii) niacin and related compounds, such as nicotinyl alcohol, nicotinamide, and nicotinic acid or a salt thereof, in an immediate release or extended release form, which may optionally be in the form of a combination with a DP-1 antagonist, such as laropiprant, (iii) PPARα agonists, such as gemfibrozil and fenofibric acid derivatives (fibrates), including clofibrate, fenofibrate, bezafibrate, ciprofibrate, and etofibrate, (iv) acyl CoA:cholesterol acyltransferase (ACAT) inhibitors, such as avasimibe and melinamide, and including selective ACAT-1 and ACAT-2 inhibitors and dual inhibitors, (v) phenolic anti-oxidants, such as probucol, (vi) microsomal triglyceride transfer protein (MTP)/ApoB secretion inhibitors, (vii) anti-oxidant vitamins, such as vitamins C and E and beta carotene, (viii) thyromimetics, (ix) LDL (low density lipoprotein) receptor inducers, (x) platelet aggregation inhibitors, for example glycoprotein IIb/IIIa fibrinogen receptor antagonists and aspirin, (xi) vitamin B12 (also known as cyanocobalamin), (xii) folic acid or a pharmaceutically acceptable salt or ester thereof, such as the sodium salt and the methylglucamine salt, (xiii) FXR and LXR ligands, including both inhibitors and agonists, (xiv) agents that enhance ABCA1 gene expression, (xv) ileal bile acid transporters, and (xvi) niacin receptor agonists (e.g. acipimox and acifran) and partial agonists.

Finally the compound of formula I can be combined with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these diseases, allowing for the possibility of administering reduced doses of active ingredients, such as doses that otherwise might be sub-therapeutic.

Examples of other active ingredients that may be administered in combination with a compound of formula I include, but are not limited to, compounds that are primarily antidiabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, LY-818, and compounds described in WO 02/060388, WO 02/08188, WO 2004/019869, WO 2004/020409, WO 2004/020408, and WO2004/066963);

(b) biguanides such as metformin, phenformin, and pharmaceutically acceptable salts thereof, in particular metformin hydrochloride and extended release formulations thereof, such as Glumetza™, Fortamet™, and GlucophageXR™;

(c) protein tyrosine phosphatase-1B (PTP-1B) inhibitors, such as ISIS-113715 and TTP814;

(d) dipeptidyl peptidase IV (DP-IV) inhibitors, including sitagliptin, vildagliptin, saxagliptin, alogliptin, linagliptin, dutogliptin, teneligliptin, MK-3102, and gemigliptin;

(e) insulin or insulin mimetics, such as for example insulin lispro, insulin glargine, insulin detemir, insulin glulisine, insulin degludec, SBS1000, insulin zinc suspension, and oral and inhalable formulations of insulin and insulin analogs;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 mimetics, GLP-1 analogs, and GLP-1 receptor agonists, such as exendins, e.g. exenatide (BYETTA), dulaglutide, semaglutide, albiglutide, liraglutide, lixisenatide, and taspoglutide, including intranasal, tranxsdermal, and once weekly formulations thereof, and oxyntomodulin analogs and derivatives, and non-peptidyl GLP-1 receptor agonists;

(l) GIP-1;

(m) amylin and amylin analogs (e.g. pramlintide);

(n) Non-sulfonylurea insulin secretagogues, such as the meglitinides (e.g. glimepiride, mitiglinide, meglitinide, nateglinide, and rapeglinide); and (o) leptin and leptin derivatives and agonists.

Preferred combinations with antidiabetic compounds include combinations of the compounds disclosed herein with DP-IV inhibitors (sitagliptin, vildagliptin, saxagliptin, alogliptin, linagliptin, dutogliptin, teneligliptin, omarigliptin, and gemigliptin), combinations with biguanides, and combinations with both a DP-IV inhibitor and a biguanide. The preferred DP-IV inhibitor is sitagliptin, and the preferred biguanide is metformin in the formulations and salt forms described above.

Other active ingredients that may be used in combination with the compound of formula I include antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and $\beta_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compound of formula I. Examples of antihypertensive compounds that may be used with the compound of formula I include thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S), 5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); and nitrates or nitric oxide donating compounds, e.g. isosorbide mononitrate.

Preferred antihypertensives that may be used in combination with the CETP inhibitors disclosed herein include one or more of an angiotensin II antagonist (losartan), an ACE inhibitor (enalapril or captopril), and hydrochlorothiazide.

Anti-obesity compounds may be administered in combination with the compounds of Formula I, including: (1) growth hormone secretagogues and growth hormone secretagogue receptor agonists/antagonists, such as NN703 and hexarelin; (2) protein tyrosine phosphatase-1B (PTP-1B) inhibitors; (3) cannabinoid receptor ligands, such as cannabinoid CB1 receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14] Bn(6-14) and [D-Phe6,Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of Formula I may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

Assays

Protocol: Scintillation Proximity Assay (SPA) for CETP Activity

First, low density lipoprotein (LDL) (Meridian) was biotinylated by incubating LDL with biotin for 1 hour on ice, after which it was dialyzed to remove free biotin. Then compounds at varying concentrations were incubated with 15 nM CETP (reagent production group, In Vitro Pharmacology, MRL Rahway) and 50 ug/ml of the biotinylated LDL in 50 mM HEPES, 150 mM NaCl, pH 7.4, for 1 hour at 37° C. The reaction was started by adding $^3$H-cholesterol ester high density lipoprotein (HDL) (American Radiochemicals Corp) at a concentration of ~0.6 nM. The reaction proceeded for 2 hours at 37° C., after which time it was quenched by the addition of 12% acetic acid. PVT streptavadin-coated scintillation proximity beads, which had been brought to room temperature, were then added at a concentration of 4 mg/ml. The assay was then mixed and counted after one half hour in a Microbeta plate reader.

In Vitro Radioactive Assays of CETP-Catalyzed CE and TG Transfer (RTA Assay)

Reagents and sources are: [3H] cholesteryl oleate (GE #TRK.886), [3H] Triolein (Perkin-Elmer NET-431), Butylated hydroxyl toluene (Aldrich, #D4740-4), DOPC (Sigma, #P6354), Sodium Bromide (Fisher scientific #S255-500), PEG 8000 (Fisher, #BP233-1), and human HDL (Intracel Corp #RP-036).

An in vitro assay for determining $IC_{50}$'s to identify compounds that inhibit CETP transfer activity is performed based on a modification of a published method (Morton and Zilversmit, (1981) A plasma inhibitor of triglyceride and cholesteryl ester transfer activities, J. Biol. Chem. 256(23), 11992-11995). The ability of inhibitors to alter CETP activity is performed using two different assays: one using recombinant CETP and one using an endogenous plasma source of CETP. Both assays measure the transfer of [3H] cholesteryl oleate or [3H] triolein from exogenous LDL to HDL.

Radiolabeled donor particles are generated by first combining 100 μl of 200 μM butylated hydroxyl toluene in $CHCl_3$, 216 μL of 21.57 mM DOPC in EtOH, and either 500 μCi [3H]-triolein (Perkin Elmer #NET-431) or 500 μCi [3H]-cholesteryl oleate (GE #TRK886) in a glass tube. Reagents are mixed, dried under nitrogen, and then resuspended in 2 mL of 50 mM Tris, 27 μM EDTA at pH 7.4. After a brief vortex, the solution is sonicated until clear and mixed with 20 mL of fresh human serum. The mixture is incubated overnight at 37° C. The [3H] labeled LDL substrate is separated at 1.063 g/ml density by sequential ultracentrifugal flotation in NaBr according to the method of Havel, Eder, et al., 1955, and Chapman, Goldstein, et al., 1981. Once isolated the particles are dialyzed 3× in CETP buffer (50 mM Tris, pH 7.4, 100 mM NaCl, 1 mM EDTA). Human HDL is purchased from Intracel and used as the acceptor particles.

Transfer assays are performed in a 96-well v-bottom polypropylene plate. For the RTA using recombinant CETP (2% RTA), an assay cocktail is prepared with the final concentrations 128 μg/mL HDL, 20 nM rCETP, 2% human serum, and 1×CETP buffer. 1 μL of each test compound diluted in DMSO is added to 47 μL of assay cocktail per well and incubated at 37° C. for 1 hour. To initiate the transfer reaction, 2 μL radiolabeled LDL is added. After an additional 60 min of incubation at 37° C., the transfer action is terminated by precipitation of LDL with an equal volume of 20% W/V PEG 8000. The plates are centrifuged at 2000 rpm for 30 minutes at 4° C. A 40 μL aliquot of the HDL-containing supernatant is transferred to a Packard Optiplate™ with 200 μL of MicroScint™ 20. After mixing, plates are counted by liquid scintillation. Counts present in the supernatant for blanks (wells containing only HDL acceptor, CETP buffer and DMSO) are subtracted from those containing test compounds and used to correct for non-specific transfer.

For the transfer assay using endogenous CETP from serum (95% RTA), the same procedure is used except that human serum is added such that a final concentration of serum of 95% of the total assay volume is achieved, yielding a concentration of approximately 15 nM endogenous CETP in the assay. This is then combined with HDL and CETP buffer and the reaction proceeds as above and is terminated as described.

Comparison of the counts of samples with inhibitors to an uninhibited (DMSO only) positive control yield a percent inhibition. A plot of percent inhibition vs. log of inhibitor concentration, fit to a Sigmoidal 4 parameter equation is used to calculate IC50.

EXAMPLES

The following schemes and examples are provided so that the invention will be more fully appreciated and understood. These schemes and examples are illustrative and are not to be construed as limiting the invention in any way. The claims appended hereto define the scope of the invention. When compounds of Formula I or compounds of the invention are mentioned herein, such compounds include compounds defined generically by Formula I and also the specific examples disclosed herein.

Starting materials are commercially available or are made using known procedures or as shown below. The examples may be synthesized according to the general schemes provided below and by using the synthetic intermediates that are described. The data reported for the examples below were generally obtained using the RTA assay in 95% human serum. The IC50's for the examples using this assay are in the range of about 30-10,000 nM. Preferred compounds have an $IC_{50}$ less than 10,000 nM, and preferably less than about 1000 nM. More preferred compounds have an IC50 less than about 500 nM. The specific compounds that are disclosed as examples have $IC_{50}$ values as defined above, or are stereoisomers of compounds that have such IC50 values. They were made as disclosed, and they inhibit CETP or are stereoisomers of CETP inhibitors as shown by the assay data that were obtained for the individual compounds.

Synthetic Schemes

Scheme A1

Synthesis of 5-bis(trifluoromethyl)phenyl)-6-(2-chloro-5-(trifluoromethyl)phenyl)-3a,4,5,6-tetrahydro-3H-cyclopenta[c]isoxazole intermediate A1 is outlined in Scheme A1. (Z)-4-(3,5-bis(trifluoromethyl)phenyl)but-3-en-1-yl trifluoromethanesulfonate 3 was synthesized in three steps. A Sonogashira coupling reaction between 1-bromo-3,5-bis(trifluoromethyl)benzene and but-3-yn-1-ol, followed by partial hydrogenation gave (Z)-4-(3,5-bis(trifluoromethyl)phenyl)but-3-en-1-ol 2. The product was then converted to (Z)-4-(3,5-bis(trifluoromethyl)phenyl)but-3-en-1-yl trifluoromethanesulfonate 3 by treatment with triflic anhydride and pyridine. Alkylation of 2-(2-chloro-5-(trifluoromethyl)phenyl)-N-methoxy-N-methylacetamide with triflate 3, followed by DIBAL reduction, afforded aldehyde 6, which was converted to oxime 7. Upon treatment with NCS and TEA, 7 underwent intramolecular 2+3 cycloaddition to give intermediate A1 as a racemic mixture.

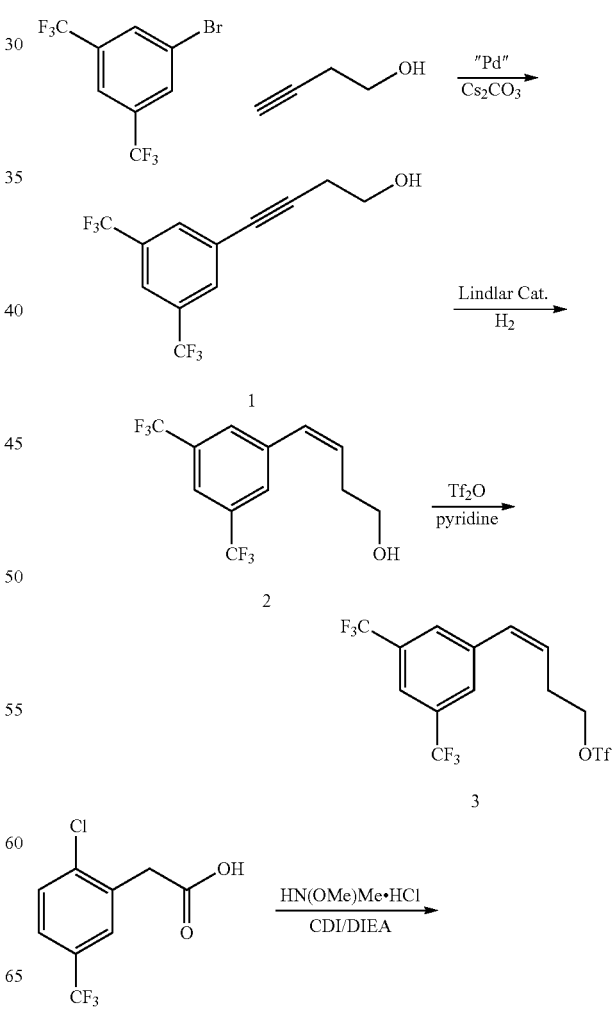

Scheme A1

-continued

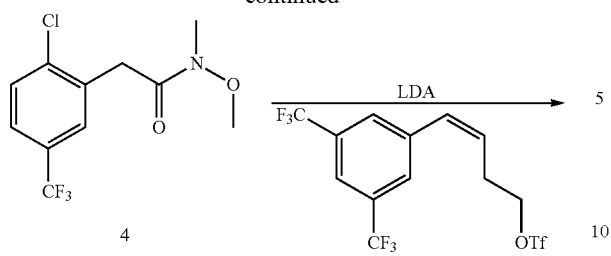

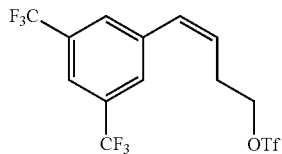

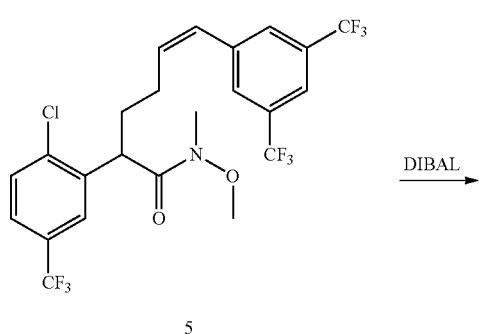

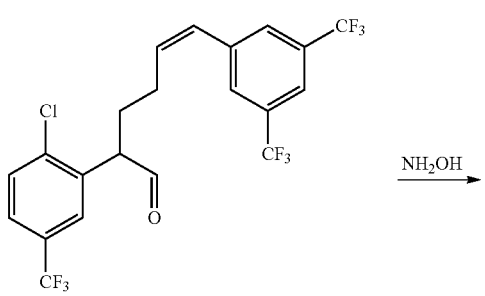

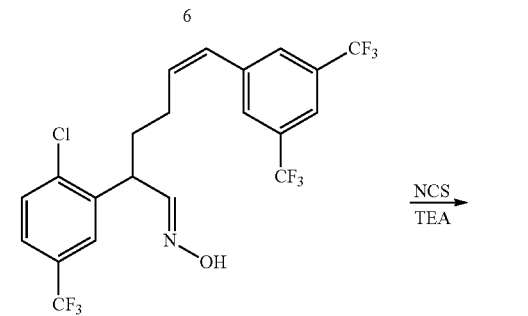

Compound 3

(Z)-4-(3,5-bis(trifluoromethyl)phenyl)but-3-en-1-yl trifluoromethanesulfonate

Step 1:

To a 250 ml RBF were added 3-butyn-1-ol (500 mg, 7.13 mmol), 3,5-bis(trifluoromethyl)bromobenzene (2.3 g, 7.9 mmol), $Cs_2CO_3$ (7.0 g, 21.4 mmol), $PdOAc_2$ (160 mg, 0.71 mmol), 2-dicyclohexylphosphino-2'-(N,N-dimethylamino) biphenyl (561 mg, 1.43 mmol), and acetonitrile (25 mL). The palladium catalyst and ligand are represented as "Pd" in Scheme A1. The mixture was stirred at 80° C. for 2 hours. It was cooled down to room temperature, diluted with EtOAc (100 mL), and washed with water and 10% HCl. The organic layer was concentrated and purified by normal phase column chromatography to yield 4-(3,5-bis(trifluoromethyl) phenyl)but-3-yn-1-ol as a yellow solid.). $^1$H NMR (500 MHz, $CDCl_3$) δ 7.87 (s, 2H), 7.8 (s, 1H), 3.89 (m, 2H), 2.76 (m, 2H).

Step 2:

To a 250 mL RBF were added 4-(3,5-bis(trifluoromethyl) phenyl) but-3-yn-1-ol (4.9 g, 17.4 mmol) and Lindlar catalyst (0.18 g, 0.86 mmol), followed by EtOH (20 ml). The reaction mixture was stirred under an $H_2$ atmosphere from a balloon at room temperature overnight. NMR showed when the reaction was complete. The reaction mixture was filtered through a pad of Celite. The filtrate was concentrated, and the residue was purified by normal phase column chromatography to yield (Z)-4-(3,5-bis(trifluoromethyl)phenyl)but-3-en-1-ol as a yellow oil. $^1$H NMR (500 MHz, $CDCl_3$) δ 7.78 (m, 3H), 6.64 (d, J=11.6 Hz, 1H), 5.70 (m, 1H), 3.82 (m, 2H), 2.60 (m, 2H).

Step 3:

To a 100 mL RBF was added (Z)-4-(3,5-bis(trifluoromethyl)phenyl) but-3-en-1-ol (4.3 g, 15.1 mmol, dissolved in 50 mL DCM). $Tf_2O$ (3.1 ml, 18.2 mmol) was added at 0° C., followed by pyridine (1.22 mL, 15.1 mmol). TLC and NMR showed when reaction was complete. Volatiles were removed. Residue was dissolved in EtOAc, and the product was washed sequentially with 1N HCl, then saturated $NaHCO_3$. The organic layer was dried over $Na_2SO_4$ and concentrated to give (Z)-4-(3,5-bis(trifluoromethyl)phenyl) but-3-en-1-yl trifluoromethanesulfonate as a brown oil. It was used directly in the next step. $^1$H NMR (500 MHz, $CDCl_3$) δ 7.83 (s, 1H), 7.70 (s, 2H), 6.78 (d, J=11.5 Hz, 1H), 5.89 (m, 1H), 4.63 (m, 2H), 2.80 (m, 2H).

Intermediate A1

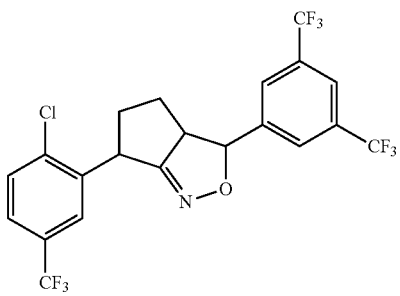 [SMILES: FC(F)(F)c1cc(C2ON=C3C(c4cc(C(F)(F)F)ccc4Cl)CCC32)cc(C(F)(F)F)c1]

3-(3,5-bis(trifluoromethyl)phenyl)-6-(2-chloro-5-(trifluoromethyl)phenyl)-3a,4,5,6-tetrahydro-3H-cyclopenta[c]isoxazole Step 1:

To a 100 ml RBF were added nBuLi (5.8 ml, 9.3 mmol) and dry THF. Diisopropylamine (1.39 ml, 9.8 mmol) was added at 0° C. under $N_2$. After stirring for 10 minutes, the mixture was cooled to −78° C. A THF solution of 2-(2-chloro-5-(trifluoromethyl)phenyl)-N-methoxy-N-methylacetamide (2.5 g, 8.9 mmol) was added. After the reaction mixture was stirred at −78° C. for 20 min, (Z)-4-(3,5-bis(trifluoromethyl)phenyl)but-3-en-1-yl trifluoromethanesulfonate (3.33 g, 7.99 mmol) was added. The reaction mixture was allowed to warm to room temperature and was stirred at room temperature for 1 hour. The reaction mixture was diluted with EtOAc, washed with saturated $NH_4Cl$, and concentrated. The residue was purified by normal phase column chromatography to yield (Z)-6-(3,5-bis(trifluoromethyl)phenyl)-2-(2-chloro-5-(trifluoromethyl)phenyl)-N-methoxy-N-methylhex-5-enamide as a yellow oil. $^1$H NMR (500 MHz, $CDCl_3$) δ 7.75 (s, 1H), 7.69 (s, 1H), 7.67 (s, 2H), 7.50 (d, J=8.3 Hz, 1H), 7.44 (d, J=8.3 Hz, 1H), 6.50 (d, J=11.4 Hz, 1H), 5.88 (m, 1H), 3.50 (s, 3H), 3.15 (s, 3H), 2.40 (m, 1H), 2.30 (m, 2H), 1.85 (m, 1H). [M+H]+ 548, found 547.96.

Step 2:

To a 100 mL RBF was added (Z)-6-(3,5-bis(trifluoromethyl)phenyl)-2-(2-chloro-5-(trifluoromethyl)phenyl)-N-methoxy-N-methylhex-5-enamide (1.7 g, 3.10 mmol) in THF. DIBAL (3.72 ml, 3.72 mmol) was added at 0° C. The mixture was stirred at room temperature until NMR showed that there was no starting material left. It was quenched by addition of 1N HCl, extracted with EtOAc, concentrated, and purified by normal phase column chromatography to yield (Z)-6-(3,5-bis(trifluoromethyl)phenyl)-2-(2-chloro-5-(trifluoromethyl)phenyl)hex-5-enal as a colorless oil. $^1$H NMR (500 MHz, $CDCl_3$) δ 9.79 (s, 1H), 7.8 (s, 1H), 7.76 (s, 1H), 7.60 (s, 2H), 7.58 (d, J=8.3 Hz, 1H), 7.47 (d, J=8.3 Hz, 1H), 6.55 (d, J=11.7 Hz, 1H), 5.82 (m, 1H), 4.18 (m, 1H), 2.58 (m, 1H), 2.38 (m, 2H), 1.95 (m, 1H).

Step 3:

To a 100 mL RBF were added (Z)-6-(3,5-bis(trifluoromethyl)phenyl)-2-(2-chloro-5-(trifluoromethyl)phenyl)hex-5-enal (600 mg, 1.23 mmol), hydroxylamine hydrochloride (341 mg, 4.91 mmol), pyridine (0.60 mL, 7.4 mmol), and DCM. The reaction mixture was stirred at room temperature for 15 min. NMR and LCMS showed a clean product. Volatiles were removed. The residue was purified by normal phase column chromatography to yield (1E,5Z)-6-(3,5-bis(trifluoromethyl)phenyl)-2-(2-chloro-5-(trifluoromethyl)phenyl)hex-5-enal oxime as white solid. [M+H]+ calculated: 504, found 503.9.

Step 4:

To a 20 mL vial were added (1E,5Z)-6-(3,5-bis(trifluoromethyl)phenyl)-2-(2-chloro-5-(trifluoromethyl)phenyl)hex-5-enal oxime (35 mg, 0.069 mmol) and NCS (11.1 mg, 0.083 mmol, dissolved in DMF). The reaction mixture was stirred at room temperature. NMR indicated that the starting material was consumed. TEA (0.25 ml, 1.78 mmol) in DCM was added dropwise. The resulting reaction mixture was stirred at room temperature for 10 min. LCMS showed the desired clean product. Volatiles were removed. Residue was purified by prep-TLC to yield intermediate A1 as a racemic mixture. $^1$H NMR (500 MHz, $CDCl_3$) δ 7.88 (s, 1H), 7.78 (s, 2H), 7.52 (m, 3H), 5.98 (d, J=9.9 Hz, 1H), 4.54 (m, 1H), 4.26 (m, 1H), 2.90 (m, 1H), 2.14 (m, 1H), 1.93 (m, 1H), 1.00 (m, 1H). [M+H]+ calculated: 501, found 501.8.

Scheme A2

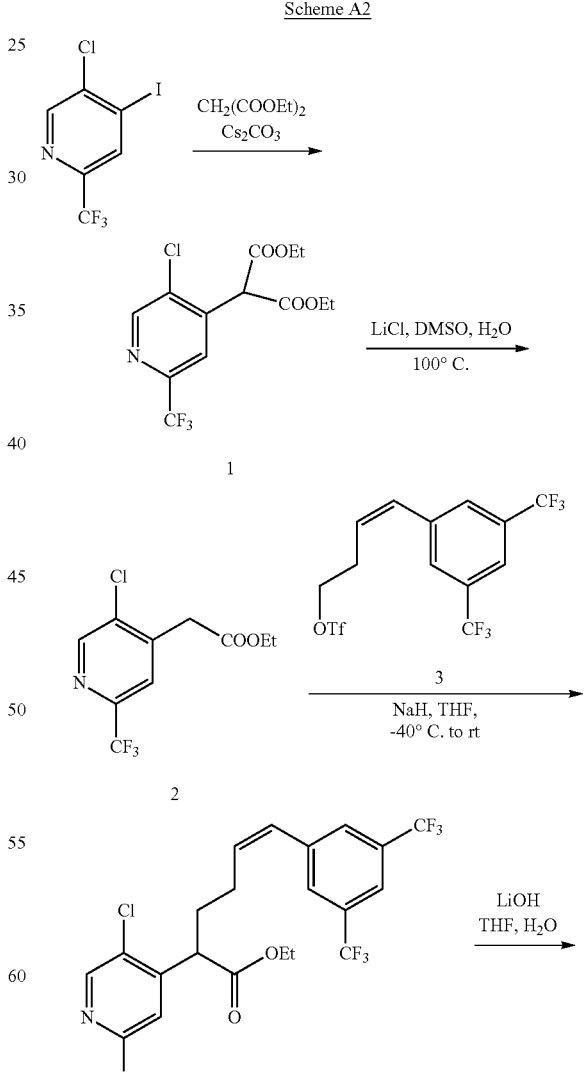

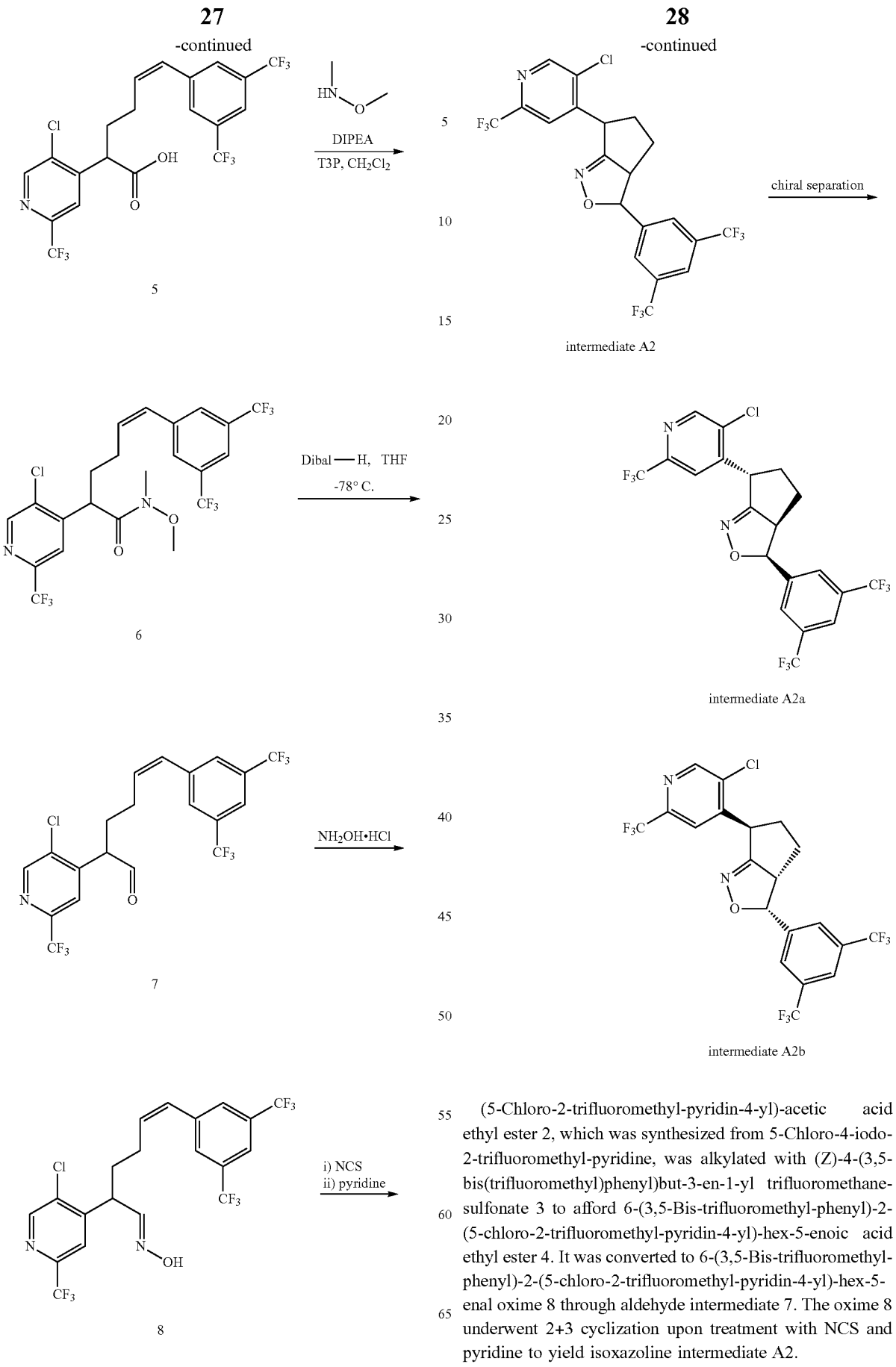

(5-Chloro-2-trifluoromethyl-pyridin-4-yl)-acetic acid ethyl ester 2, which was synthesized from 5-Chloro-4-iodo-2-trifluoromethyl-pyridine, was alkylated with (Z)-4-(3,5-bis(trifluoromethyl)phenyl)but-3-en-1-yl trifluoromethane-sulfonate 3 to afford 6-(3,5-Bis-trifluoromethyl-phenyl)-2-(5-chloro-2-trifluoromethyl-pyridin-4-yl)-hex-5-enoic acid ethyl ester 4. It was converted to 6-(3,5-Bis-trifluoromethyl-phenyl)-2-(5-chloro-2-trifluoromethyl-pyridin-4-yl)-hex-5-enal oxime 8 through aldehyde intermediate 7. The oxime 8 underwent 2+3 cyclization upon treatment with NCS and pyridine to yield isoxazoline intermediate A2.

Intermediate A2a and A2b

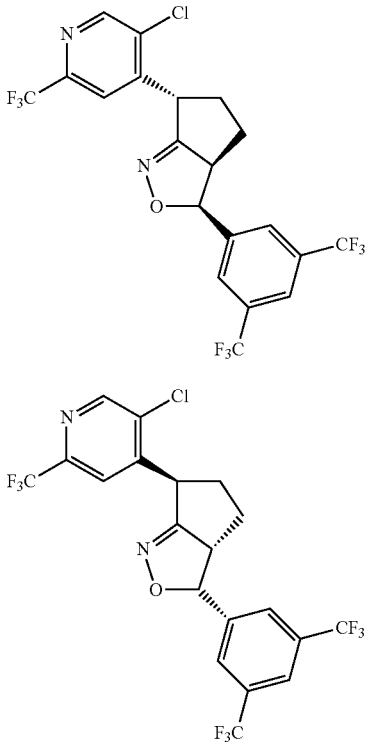

(3S,3aR,6S)-3-(3,5-bis(trifluoromethyl)phenyl)-6-(5-chloro-2-(trifluoromethyl)pyridin-4-yl)-3a,4,5,6-tetrahydro-3H-cyclopenta[c]isoxazole A2a and (3R,3aS,6R)-3-(3,5-bis(trifluoromethyl)phenyl)-6-(5-chloro-2-(trifluoromethyl)pyridin-4-yl)-3a,4,5,6-tetrahydro-3H-cyclopenta[c]isoxazole A2b Step 1:

To a solution of 5-Chloro-4-iodo-2-trifluoromethyl-pyridine (7.25 g, 23.6 mmol) in DMSO (70.0 mL) were added diethylmalonate (4.53 g, 28.3 mmol) and cesium carbonate (11.52 g, 35.3 mmol). The reaction mixture was stirred at 100° C. for 5 h. Reaction completion was confirmed by TLC. Upon cooling, the reaction mixture was diluted with water and extracted with ethyl acetate. The organic layer was washed with brine, dried over anhydrous sodium sulfate, filtered and concentrated under reduced pressure. Crude product was purified by flash column chromatography on silica gel eluting with 10-20% ethyl acetate/hexanes to yield diethyl 2-(5-Chloro-2-trifluoromethyl-pyridin-4-yl)-malonic acid diethyl ester 1. MS ESI/APCI calc'd. for $C_{13}H_{13}ClF_3NO_4$ [M+H]$^+$ 339.7, found 340.2.

Step 2:

To a stirred solution of diethyl 2-(5-chloro-2-(trifluoromethyl) pyridin-4-yl)malonate 1 (5.0 g, 14.7 mmol) in DMSO was added LiCl in water. The resulting solution was stirred at 100° C. overnight. The reaction was complete as confirmed by TLC. Upon cooling, the reaction mixture was diluted with water and extracted with ethyl acetate. The organic layer was washed with brine, dried over anhydrous sodium sulfate, filtered and concentrated under reduced pressure to give (5-Chloro-2-trifluoromethyl-pyridin-4-yl)-acetic acid ethyl ester 2. The crude product was used directly in the next step. MS ESI/APCI calc'd. for $C_{10}H_9ClF_3NO_2$ [M+H]$^+$ 267.6, found 268.0.

Step 3:

To a stirred solution of (5-Chloro-2-trifluoromethyl-pyridin-4-yl)-acetic acid ethyl ester 2 (3.6 g, 13.45 mmol) in THF (150 mL) was added NaH (0.97 g, 24.2 mmol) under nitrogen at 0° C. The resulting mixture was stirred for 45 minutes, then 4-(3,5-bis-trifluoromethyl-phenyl)-but-3-enyl ester 3 (6.71 g, 16.1 mmol) in THF was added to the above reaction mixture at −40° C. The resulting mixture was stirred for 2 h at the same temperature. Reaction completion was confirmed by TLC analysis. The reaction mixture was then quenched with ice water. The resulting mixture was extracted with ethyl acetate twice. Combined extracts were washed with brine, dried over anhydrous sodium sulfate, filtered and concentrated under reduced pressure. The crude product was purified by flash silica gel column chromatography to afford 6-(3,5-Bis-trifluoromethyl-phenyl)-2-(5-chloro-2-trifluoromethyl-pyridin-4-yl)-hex-5-enoic acid ethyl ester 4. $^1$H NMR (400 MHz, CDCl$_3$): δ 8.63 (s, 1H); 7.75 (s, 1H); 7.66 (s, 1H); 7.63 (s, 2H); 6.54 (d, J=11.6 Hz, 1H); 5.87-5.80 (m, J=6.68 Hz, 1H); 4.32-4.28 (m, 1H); 4.14 (q, J=8.00, 2H); 2.41-2.34 (m, 3H); 2.00-1.91 (m, 1H); 1.21 (t, J=8.00 Hz, 3H). MS ESI/APCI calc'd. for $C_{22}H_{17}ClF_9NO_2$ [M+H]$^+$ 534.08, found 534.2.

Step 4:

To a stirred solution of 6-(3,5-Bis-trifluoromethyl-phenyl)-2-(5-chloro-2-trifluoromethyl-pyridin-4-yl)-hex-5-enoic acid ethyl ester 4 (5.1 g, 9.55 mmol) in THF/H$_2$O (100 mL, 1:1) was added LiOH.H$_2$O at room temperature. The resulting mixture was stirred overnight. Reaction completion was confirmed by TLC analysis. Solvent was removed at the reduced pressure. Residue was diluted with ethyl acetate (250.0 ml). After pH was adjusted to 5-6 with citric acid solution, the reaction mixture was washed with water (50.0 ml), then brine solution, then was dried over anhydrous sodium sulfate, filtered and concentrated under reduced pressure to afford 6-(3,5-Bis-trifluoromethyl-phenyl)-2-(5-chloro-2-trifluoromethyl-pyridin-4-yl)-hex-5-enoic acid 5 as a solid. This crude product was used directly in the next step.

Step 5:

To a stirred solution of 6-(3,5-Bis-trifluoromethylphenyl)-2-(5-chloro-2-trifluoromethyl-pyridin-4-yl)-hex-5-enoic acid 5 (4.42 g, 8.73 mmol) in dichloromethane (40 mL) were added N,O-dimethylhydroxylamine hydrochloride (1.27 g, 13.1 mmol) followed by N,N-Diisopropylethylamine (11.1 mL, 26.21 mmol). The resulting mixture was stirred for 15 minutes. T3P was then added slowly at room temperature. The reaction mixture was stirred for 3 hrs at room temperature. Reaction completion was confirmed by TLC analysis. Reaction mixture was diluted with water (100.0 ml) and was extracted with DCM twice. Combined organics were washed with brine solution, dried over Na$_2$SO$_4$, filtered and concentrated under reduced pressure. Crude product was purified by flash column chromatography on silica gel eluting with 7-11% ethyl acetate/hexanes to yield (Z)-6-(3,5-bis(trifluoromethyl)phenyl)-2-(5-chloro-2-(trifluoromethyl)pyridin-4-yl)-N-methoxy-N-methylhex-5-enamide 6. $^1$H NMR (300 MHz, CDCl$_3$): δ 8.64 (s, 1H); 7.74-7.64 (m, 4H); 6.52-6.49 (d, J=11.6 Hz, 1H); 5.88-5.80 (m, 1H); 4.57 (t, J=8.00 Hz, 1H); 3.58 (s, 3H); 3.13 (s, 3H); 2.42-2.21 (m, 3H); 1.85-1.80 (m, 1H). MS ESI/APCI calc'd. for $C_{22}H_{18}ClF_9N_2O_2$ [M+H]$^+$ 549.1, found 549.2.

Step 6:

To the stirred solution of (Z)-6-(3,5-bis(trifluoromethyl)phenyl)-2-(5-chloro-2-(trifluoromethyl)pyridin-4-yl)-N-methoxy-N-methylhex-5-enamide 6 (3.2 g, 5.83 mmol) in THF (35 mL) was added DIBAL-H in THF (1M, 11.66 mL) dropwise at −78° C. The resulting solution was stirred for 2 h at same temperature. Reaction completion was confirmed by TLC analysis. Reaction mixture was quenched with NH$_4$Cl solution, extracted with ethyl acetate twice. Combined organic layers were washed with brine solution, dried over Na$_2$SO$_4$ and concentrated under reduced pressure. The crude aldehyde product 6-(3,5-Bis-trifluoromethyl-phenyl)-2-(5-chloro-2-trifluoromethyl-pyridin-4-yl)-hex-5-enal 7 was used for the next step without further purification. MS ESI/APCI calc'd. for C$_{20}$H$_{13}$ClF$_9$NO [M−H]$^+$ 488.1, found 488.0.

Step 7:

To a stirred solution of 6-(3,5-Bis-trifluoromethylphenyl)-2-(5-chloro-2-trifluoromethyl-pyridin-4-yl)-hex-5-enal 7 (3.1 g, 6.32 mmol) in methanol (60 mL) were added hydroxylamine hydrochloride (1.75 g, 25.3 mmol) and pyridine (3.16 mL) at room temperature. The resulting mixture was stirred for 2 h. The completion of reaction was confirmed by TLC analysis. Solvent was removed under reduced pressure. Residue was dissolved in ethyl acetate (500 mL) and washed sequentially with aqueous citric acid solution, water, and brine solution. Organics were dried over sodium sulfate, filtered and concentrated under reduced pressure. The crude (1E,5Z)-6-(3,5-bis(trifluoromethyl)phenyl)-2-(5-chloro-2-(trifluoromethyl)pyridin-4-yl)hex-5-enal oxime 8 obtained was used directly in the next step.

Step 8:

To a stirred solution of 6-(3,5-Bis-trifluoromethyl-phenyl)-2-(5-chloro-2-trifluoromethyl-pyridin-4-yl)-hex-5-enal oxime 8 (2.95 g, 5.84 mmol) in chloroform (60.0 mL) was added NCS (1.01 g, 7.59 mmol). After 5 minutes of stirring, pyridine (0.53 mL) was added to the reaction mixture. The resulting solution was stirred for 1 hr at room temperature. The completion of reaction was confirmed by TLC analysis. Reaction mixture was diluted with DCM, washed with water twice, and then with brine solution. Organics were dried over Na$_2$SO$_4$, filtered and concentrated. Residue was purified by flash silica column chromatography to afford 3-(3,5-Bis-trifluoromethyl-phenyl)-6-(5-chloro-2-trifluoromethyl-pyridin-4-yl)-3a,4,5,6-tetrahydro-3H-cyclopenta[c]isoxazole intermediate A2 as a racemic mixture. It was further separated by chiral preparative HPLC (Method—Column: CHIRAL CEL OD-H 250×4.6 mm 5μ; mobile phase: 0.1% TFA in hexane:ethanol (98:2); flow: 0.7 mL/min) to yield a pair of enantiomers. $^1$H NMR (400 MHz, CDCl$_3$): δ 8.69 (s, 1H); 7.87 (s, 1H); 7.75 (s, 2H); 7.55 (s, 1H); 6.02-6.00 (d, J=8.01 Hz, 1H); 4.53-4.46 (m, 1H); 4.23 (t, J=8.01 Hz, 1H); 2.98-2.91 (m, 1H); 2.14-2.04 (m, 1H); 1.97-1.90 (m, 1H); 1.04-0.99 (m, 1H). Isomer A2a: MS ESI/APCI calc'd. for C$_{20}$H$_{12}$ClF$_9$N$_2$O [M−H]$^+$ 501.05, found 501.0. Retention time: 13.01 mins. Isomer A2b: MS ESI/APCI calc'd. for C$_{20}$H$_{12}$ClF$_9$N$_2$O [M−H]$^+$ 501.05, found 501.0. Retention time: 16.85 mins.

Scheme B:

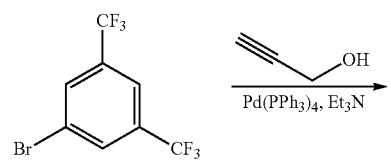

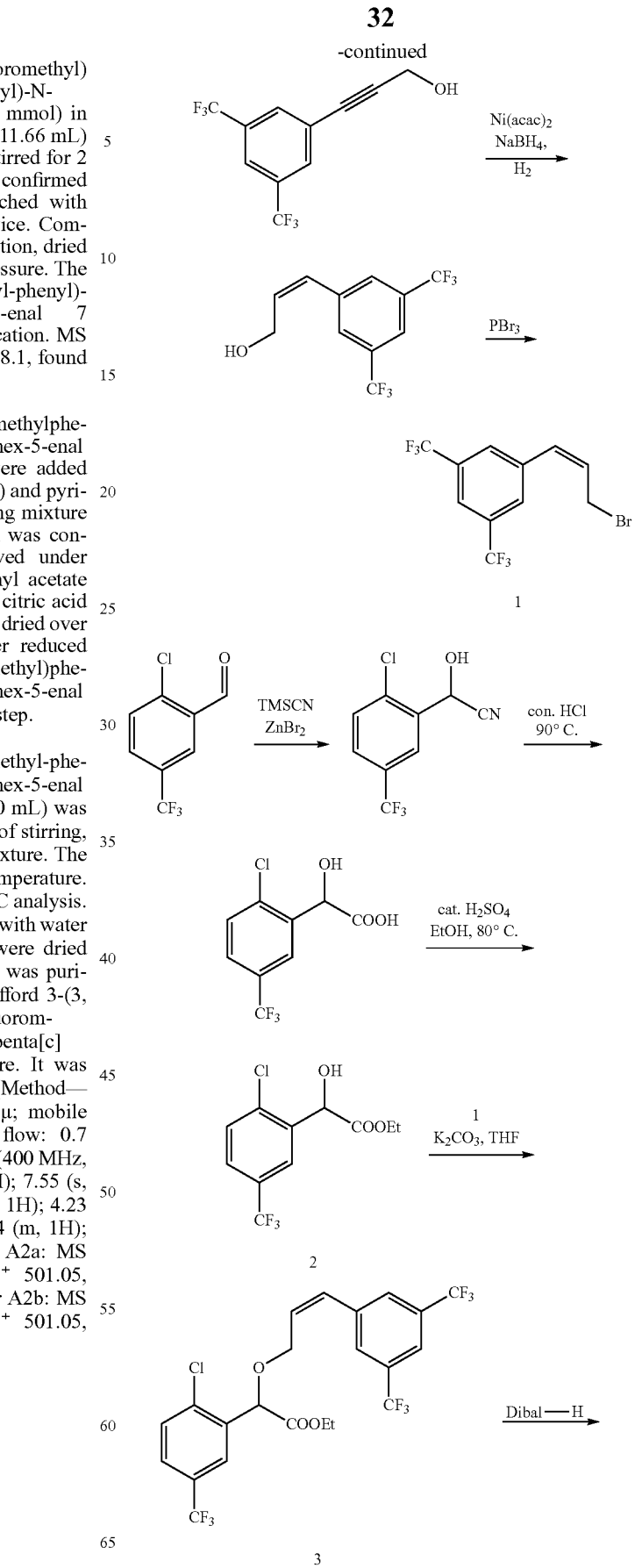

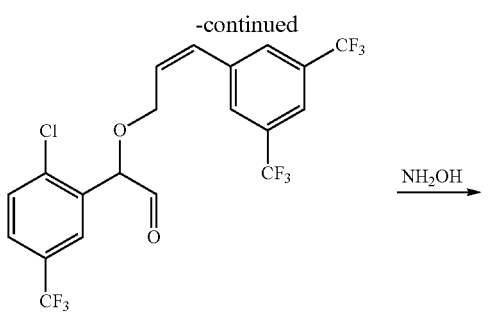

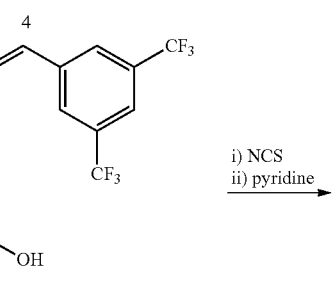

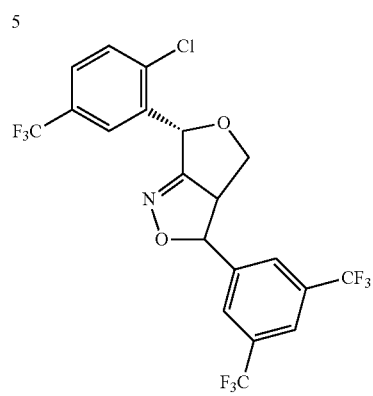

Intermediate B1

Synthesis of intermediate B1, 3-(3,5-bis(trifluoromethyl)phenyl)-6-(2-chloro-5-(trifluoromethyl)phenyl)-3a,4-dihydro-3H,6H-furo[3,4-c]isoxazole is outlined in Scheme B. Ethyl 2-(2-chloro-5-(trifluoromethyl)phenyl)-2-hydroxyacetate 1 was synthesized from 2-chloro-5-(trifluoromethyl)benzaldehyde. It was alkylated with (Z)-1-(3-bromoprop-1-en-1-yl)-3,5-bis(trifluoromethyl)benzene 2 to give ethyl (Z)-2-((3-(3,5-bis(trifluoromethyl)phenyl)allyl)oxy)-2-(2-chloro-5-(trifluoromethyl)phenyl)acetate 3. Compound 3 was further converted to the oxime 5. Upon treatment with NCS and base, oxime 5 reacted via a 2+3 cycloaddition to yield intermediate B1 as a racemic mixture.

Compound 1

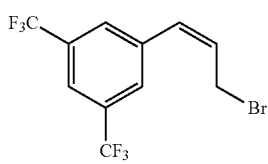 [SMILES: FC(F)(F)c1cc(/C=C\CBr)cc(C(F)(F)F)c1]

(Z)-1-(3-bromoprop-1-en-1-yl)-3,5-bis(trifluoromethyl)benzene

Step 1:

Into a 50-mL sealed tube containing a degassed solution of 1-bromo-3,5-bis(trifluoromethyl)benzene 2 (10.0 g, 34.0 mmol) in THF (50.0 mL) were added propargyl alcohol (2.6 mL, 44.0 mmol), triethylamine (50.0 mL), and tetrakis(triphenylphosphine)palladium(0) (0.985 g, 8.0 mmol). The contents were heated at 70° C. for 5 h. TLC analysis indicated complete conversion of the starting material. The reaction mixture was diluted with ethyl acetate (20 mL) and filtered through a pad of celite. The filtrate was washed with water (1×15 mL), brine (1×10 mL), dried over sodium sulfate, filtered and the filtrate was concentrated under reduced pressure to furnish the crude product, which was purified by flash column chromatography on silica gel (230-400 mesh) with 5-10% ethyl acetate/petroleum ether to furnish 3-(3,5-bis(trifluoromethyl)phenyl)prop-2-yn-1-ol as a white solid. $^1$H NMR 400 MHz, CDCl$_3$: δ 7.87 (s, 2H), 7.82 (s, 1H), 4.53 (s, 2H).

Step 2:

To a stirred solution of 3-(3,5-bis(trifluoromethyl)phenyl)prop-2-yn-1-ol (6.0 g, 22.0 mmol) in ethanol (70.0 ml), was added nickel acetate tetrahydrate (6.0 g, 3.0 mmol) followed by sodium borohydride (0.127 g, 3.0 mmol) at 0° C. The contents were stirred under an atmosphere of hydrogen (1 atm) at room temperature for 15 h. TLC analysis indicated disappearance of the starting material. The reaction mixture was diluted with ethanol (50 mL) and filtered through celite bed. The filtrate was concentrated under reduced pressure to give the crude product, which was purified by flash column chromatography on silica gel eluting with 10-20% ethyl acetate/hexanes to yield (Z)-3-(3,5-bis(trifluoromethyl)phenyl)prop-2-en-1-ol. $^1$H NMR 400 MHz, CDCl$_3$: δ 7.78 (s, 1H), 7.66 (s, 2H), 6.63 (d, J=12.00 Hz, 1H), 6.14-6.08 (m, 1H), 4.40 (dd, J=2.00, 10.40 Hz, 2H).

Step 3:

To a stirred solution of (Z)-3-(3,5-bis(trifluoromethyl)phenyl)prop-2-en-1-ol (0.2 g, 0.74 mmol) in diethylether (7.0 ml), was added a solution of tribromophosphine (0.10 g, 0.37 mmol) in diethylether (2.0 mL) at 0° C. The reaction mixture was stirred for 18 hrs at room temperature. Reaction completion was confirmed by TLC. Water was then added to the reaction mixture, and the product was extracted with ethyl acetate. Then the organic layer was washed with brine, dried over anhydrous sodium sulfate and concentrated under reduced pressure. Crude product was purified by flash column chromatography on silica gel eluting with 5-10% ethyl acetate/hexanes to yield (Z)-1-(3-bromoprop-1-en-1-yl)-3,5-bis(trifluoromethyl)benzene 1. $^1$H NMR 400 MHz, CDCl$_3$: δ 7.82 (s, 2H), 7.80 (s, 1H), 6.74-6.61 (m, 1H), 6.25-6.15 (m, 1H), 4.05 (dd, J=0.72, 11.66 Hz, 2H).

Compound 2

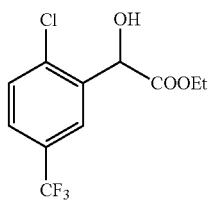 [SMILES: CCOC(=O)C(O)c1cc(C(F)(F)F)ccc1Cl]

Ethyl 2-(2-chloro-5-(trifluoromethyl)phenyl)-2-hydroxyacetate

Step 1:

To a stirred solution of 2-chloro-5-(trifluoromethyl)benzaldehyde (1.0 g, 4.8 mmol) in dichloromethane (15.0 mL) were added trimethylsilyl cyanide (0.95 g, 9.6 mmol) and zinc bromide (0.054 g, 0.24 mmol) at room temperature. The reaction mixture was heated to 50° C. overnight. Reaction completion was confirmed by TLC. Water was then added to the reaction mixture, and product was extracted with dichloromethane. The aqueous layer was extracted with dichloromethane two times. Organics were combined, washed with brine, dried over anhydrous sodium sulfate, filtered and concentrated under reduced pressure. Crude product was purified by flash column chromatography on silica gel eluting with 10-20% ethyl acetate/hexanes to yield 2-(2-chloro-5-(trifluoromethyl)phenyl)-2-hydroxyacetonitrile.
$^1$H NMR 400 MHz, CDCl$_3$: δ 8.02 (s, 1H), 7.67 (d, J=8.00 Hz, 1H), 7.60 (d, J=8.00 Hz, 1H), 5.91 (s, 1H), 3.67 (bs, 1H).

Step 2:

To a stirred solution of 2-(2-chloro-5-(trifluoromethyl)phenyl)-2-hydroxyacetonitrile (11 g, 26.7 mmol) was added concentrated hydrochloric acid at room temperature, and then the reaction mixture was heated to reflux overnight. The completion of reaction was confirmed by TLC. The reaction mixture was cooled to room temperature, and 10% sodium bicarbonate solution was added. The resulting mixture was extracted with ethyl acetate twice. The aqueous layer was reacidified with dilute hydrochloric acid and extracted with ethyl acetate. The combined organics were dried over Na$_2$SO$_4$, filtered and concentrated. Crude product was purified by flash column chromatography on silica gel eluting with 10-20% methanol/dichloromethane to yield 2-(2-chloro-5-(trifluoromethyl)phenyl)-2-hydroxyacetic acid. $^1$H NMR (400 MHz, DMSO-d$_6$): δ 12.97 (s, 1H), 7.84 (s, 1H), 7.73-7.68 (m, 2H), 6.47 (s, 1H), 5.38 (s, 1H).

Step 3:

To a stirred solution of 2-(2-chloro-5-(trifluoromethyl)phenyl)-2-hydroxyacetic acid (5.4 g, 21.2 mmol) in ethanol (50 ml) was added concentrated sulfuric acid (1.0 mL), and the resulting mixture was stirred at 80° C. for 2 hrs. Reaction completion was confirmed by TLC analysis. 10% Sodium bicarbonate was added, and the resulting mixture was extracted with ethyl acetate twice. The organics were combined, dried over Na$_2$SO$_4$ and concentrated to give ethyl 2-(2-chloro-5-(trifluoromethyl)phenyl)-2-hydroxyacetate 2. MS ESI/APCI calc'd. for C$_{11}$H$_{10}$ClF$_3$O$_3$ [M+H]$^+$ 283.0, found 283.2.

Intermediate B1

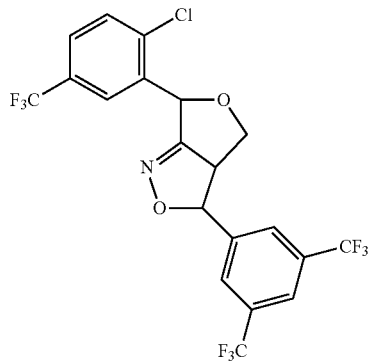 [SMILES: FC(F)(F)c1cc(C2ON=C3C(c4cc(C(F)(F)F)ccc4Cl)OCC32)cc(C(F)(F)F)c1]

3-(3,5-bis(trifluoromethyl)phenyl)-6-(2-chloro-5-(trifluoromethyl)phenyl)-3,3a,4,6-tetrahydrofuro[3,4-c]isoxazole Step 1:

To a stirred solution of ethyl 2-(2-chloro-5-(trifluoromethyl)phenyl)-2-hydroxyacetate 2 (3.8 g, 13.0 mmol) and (Z)-1-(3-bromoprop-1-en-1-yl)-3,5-bis(trifluoromethyl)benzene 1 (4.03 g, 13.0 mmol) in acetonitrile (50.0 ml) was added potassium carbonate (2.8 g, 20.0 mmol) at room temperature. The resulting reaction mixture was stirred for 18 hrs at room temperature. The reaction mixture was quenched with ice water and extracted with ethyl acetate. The organic layer was concentrated under reduced pressure, and the residue was purified by flash column chromatography on silica gel eluting with 10-20% ethyl acetate/hexanes to furnish ester compound 3. $^1$H NMR (400 MHz, CDCl$_3$): δ 7.82-7.78 (m, 2H), 7.69 (s, 2H), 7.64-7.61 (m, 2H), 6.73 (d, J=12.00 Hz, 1H), 6.16-6.08 (m, 1H), 5.37 (s, 1H), 4.45-4.39 (m, 1H), 4.28-4.26 (m, 1H), 4.23-4.14 (m, 2H), 1.24 (t, J=8.00 Hz, 3H).

Step 2:

To a solution of 3 (3.5 g, 6.5 mmol) in THF (40.0 mL) at −78° C. was added DIBAL-H (7.8 mL, 7.8 mmol), and the resulting reaction mixture was stirred at the same temperature for 1 h. TLC analysis indicated complete conversion of the starting material. The reaction mixture was diluted with ethyl acetate (15 mL), washed with water (5.0 mL), brine (5.0 mL), dried over anhydrous Na$_2$SO$_4$, filtered and concentrated. Crude product was purified by flash column chromatography on silica gel eluting with 30-50% ethyl acetate/hexanes to furnish aldehyde 4. $^1$H NMR (400 MHz, CDCl$_3$): δ 9.66 (s, 1H), 7.77 (s, 1H), 7.75-7.63 (m, 3H), 7.53-7.50 (m, 2H), 6.77 (d, J=12.00 Hz, 1H), 6.16-6.10 (m, 1H), 4.28-4.41 (m, 2H). MS ESI/APCI calc'd. for C$_{20}$H$_{12}$ClF$_9$NO$_2$ [M−H]$^+$ 489.0, found 489.2.

Step 3:

To the solution of (Z)-2-((3-(3,5-bis(trifluoromethyl)phenyl)allyl)oxy)-2-(2-chloro-5-(trifluoromethyl)phenyl)acetaldehyde 4 (50 mg, 0.10 mmol) in methanol (2.0 mL) were added pyridine (0.030 mL, 0.41 mmol) followed by hydroxylamine hydrochloride (42 mg, 0.60 mmol). The resulting reaction mixture was stirred at room temperature for 2 hrs. TLC analysis indicated complete conversion. Volatiles were removed under reduced pressure, and the crude product was purified by flash column chromatography on silica gel eluting with 20-40% ethyl acetate/hexanes to furnish oxime 5. MS ESI/APCI calc'd. for C$_{20}$H$_{13}$ClF$_9$NO$_2$ [M−H]$^+$ 504.04, found 504.2.

Step 4:

To the solution of 5 (0.050 g, 0.10 mmol) in chloroform (3.0 mL) were added N-chlorosuccinimide (17.1 mg, 0.13 mmol) followed by pyridine (0.008 mL, 0.1 mmol). The resulting reaction mixture was stirred at room temperature for 3 hrs. TLC analysis indicated complete conversion of the starting material. Reaction mixture was quenched with dilute hydrochloric acid and extracted with dichloromethane. Organics were concentrated, and the residue was purified by flash column chromatography on silica gel eluting with 20-30% ethyl acetate/hexanes to furnish intermediate B1. $^1$H NMR (400 MHz, CDCl$_3$): δ 7.88 (s, 1H), 7.61-7.59 (m, 4H), 7.49 (s, 1H), 6.02 (d, J=10.80 Hz, 1H), 5.94 (s, 1H), 4.91 (q, J=8.00 Hz, 1H), 4.25 (t, J=9.20 Hz, 1H), 3.33 (t, J=9.20 Hz, 1H), MS ESI/APCI calc'd. for C$_{20}$H$_{11}$ClF$_9$NO$_2$ [M+H]$^+$ 504.03, found 504.2.

EXAMPLES

The following schemes and examples are provided so that the invention will be more fully appreciated and understood. These schemes and examples are illustrative and are not to be construed as limiting the invention in any way. The claims appended hereto define the scope of the invention.

Scheme 1

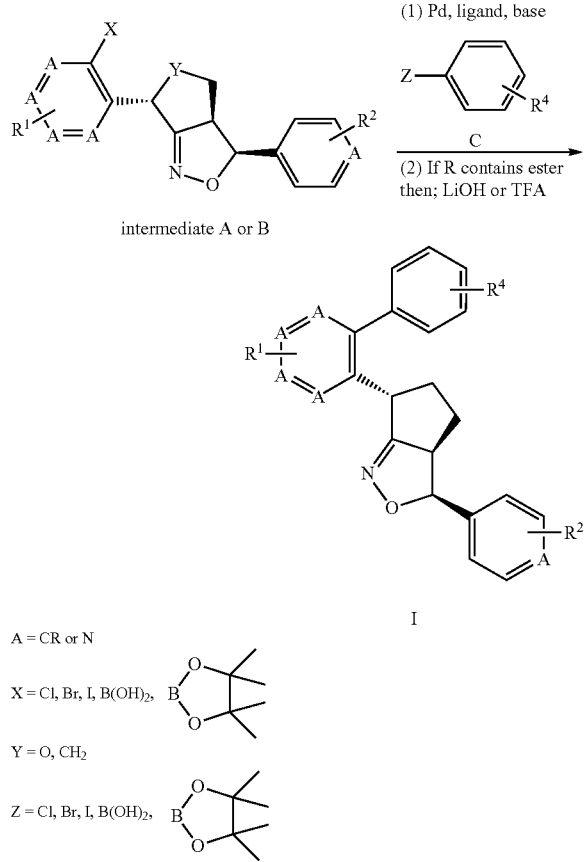

A = CR or N

X = Cl, Br, I, B(OH)₂, [pinacol boronate]

Y = O, CH₂

Z = Cl, Br, I, B(OH)₂, [pinacol boronate]

In accordance with Scheme 1, a cross-coupling reaction between Intermediate A or B and an appropriately functionalized boronic acid/ester/halide C provides compounds of the general formula (I). Some of the intermediates C were synthesized according to published procedures in WO 2012058187, WO 2013063217 and WO 2013063217. In cases where an ester group is present in the product as a protecting group for the carboxylic acid, a saponification or deprotection step may subsequently be carried out to generate the acid.

Example 1A and 1B

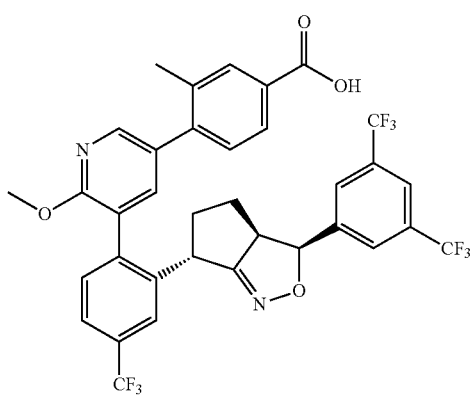

1A

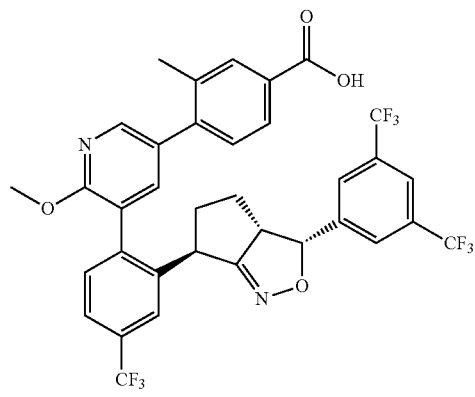

1B 4-(5-(2-((3S,3aR,6S)-3-(3,5-bis(trifluoromethyl) phenyl)-3a,4,5,6-tetrahydro-3H-cyclopenta[c]isoxazol-6-yl)-4-(trifluoromethyl)phenyl)-6-methoxy-pyridin-3-yl)-3-methylbenzoic acid 1A and 4-(5-(2-((3R,3aS,6R)-3-(3,5-bis(trifluoromethyl)phenyl)-3a, 4,5,6-tetrahydro-3H-cyclopenta[c]isoxazol-6-yl)-4-(trifluoromethyl)phenyl)-6-methoxypyridin-3-yl)-3-methylbenzoic acid 1B Step 1:

To a 5 ml RBF were added 3-(3,5-bis(trifluoromethyl) phenyl)-6-(2-chloro-5-(trifluoromethyl)phenyl)-3a,4,5,6-tetrahydro-3H-cyclopenta[c]isoxazole intermediate A1 (50 mg, 0.1 mmol), tert-butyl 4-(6-methoxy-5-(4,4,5,5-tetramethyl-1,3,2-dioxaborolan-2-yl)pyridin-3-yl)-3-methylbenzoate (51 mg, 0.12 mmol), potassium phosphate (42.3 mg, 0.199 mmol), XPhos preCatalyst (7.84 mg, 9.96 μmol), 1,4-dioxane (2 mL) and water (0.2 mL). The mixture was stirred at 90° C. for 2 hours. After cooling down, volatiles were removed. The residue was purified by silica gel column chromatography to yield the target compound as a racemic mixture. $[M-H]^+$ 763.2, found 763.3.

Step 2:

To a 10 mL scintillation vial were added tert-butyl 4-(5-(2-(3-(3,5-bis(trifluoromethyl)phenyl)-3a,4,5,6-tetrahydro-3H-cyclopenta[c]isoxazol-6-yl)-4-(trifluoromethyl)phenyl)-6-methoxypyridin-3-yl)-3-methylbenzoate (20 mg, 0.026 mmol) and DCM (0.5 ml), followed by TFA (0.81 mL, 10.5 mmol). After the reaction mixture was stirred at room temperature for 10 mins, LCMS showed all the starting material has converted. Volatiles were removed. Residue was purified by reverse phase HPLC to yield 4-(5-(2-((3S, 3aR,6S)-3-(3,5-bis(trifluoromethyl)phenyl)-3a,4,5,6-tetrahydro-3H-cyclopenta[c]isoxazol-6-yl)-4-(trifluoromethyl) phenyl)-6-methoxypyridin-3-yl)-3-methylbenzoic as a racemic mixture. The racemic mixture was separated by chiral SFC on Chiral Cel IA (4.6×250 mm) with 30% 2:1 MeOH:MeCN/CO₂ (2.1 mL/min, 100 bar, 35° C.) as the eluatant to give a pair of enantiomers with retention time of 2.16 (1A) and 2.85 mins (1B) respectively. $^1$H NMR (500 MHz, CDCl₃): δ 8.27 (d, J=2.3 Hz, 1H), 8.08 (s, 1H), 8.05 (d, J=2.3 Hz, 1H), 7.83 (s, 1H), 7.74 (s, 1H), 7.69 (s, 1H), 7.61 (s, 2H), 7.57 (s, 1H), 7.40 (d, J=2.1 Hz, 1H), 7.38 (d, J=2.1 Hz, 1H), 5.92 (d, J=10.6 Hz, 1H), 4.45 (m, 1H), 4.35 (m, 1H), 4.03 (s, 3H) 3.95. IC₅₀ RTA (95% HS): 1A: 70 nM; 1B: 10,000 nM.

Example 2B

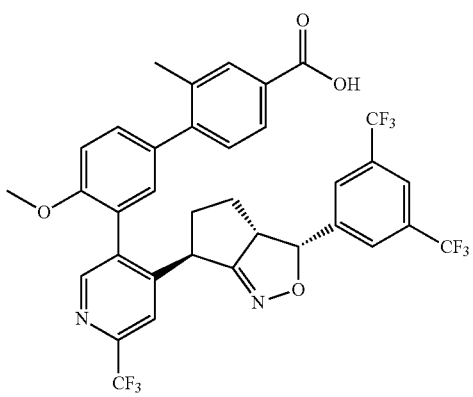 [SMILES: COc1ccc(-c2ccc(C(=O)O)cc2C)cc1-c1cnc(C(F)(F)F)cc1[C@H]1CC[C@H]2C1=NO[C@H]2c1cc(C(F)(F)F)cc(C(F)(F)F)c1]

3'-(4-((3R,3aS,6R)-3-(3,5-bis(trifluoromethyl)phenyl)-3a,4,5,6-tetrahydro-3H-cyclopenta[c]isoxazol-6-yl)-6-(trifluoromethyl)pyridin-3-yl)-4'-methoxy-2-methyl-[1,1'-biphenyl]-4-carboxylic acid Step 1:

To (3R,3aS,6R)-3-(3,5-bis(trifluoromethyl)phenyl)-6-(5-chloro-2-(trifluoromethyl)pyridin-4-yl)-3a,4,5,6-tetrahydro-3H-cyclopenta[c]isoxazole A2b (0.050 g, 0.10 mmol) were added THF (3.0 mL), water (1.0 mL), tribasic potassium phosphate (0.053 g, 0.25 mmol), (4'-(tert-butoxycarbonyl)-4-methoxy-2'-methyl-[1,1'-biphenyl]-3-yl)boronic acid (0.051 g, 0.15 mmol) and chloro(2-dicyclohexylphosphino-2',4',6'-triisopropyl-1,1'-biphenyl)[2-(2-aminoethyl)phenyl)]palladium(II) (0.004 g, 0.005 mmol). The reaction vessel was flushed with nitrogen gas and heated at 60° C. overnight. Upon cooling, the reaction mixture was diluted with ethyl acetate:hexanes (1:2, 10 mL), washed with water (10 mL). The organics were dried over sodium sulfate, filtered and concentrated. The residue was dissolved in dichloromethane (2.0 mL). Trifluoroacetic acid (0.2 mL) was added. Reaction mixture was stirred at room temperature for 3 hrs. TLC analysis indicated complete conversion of the starting material. Volatiles were removed under reduced pressure and crude product was purified by reverse phase HPLC to yield 3'-(4-((3R,3aS,6R)-3-(3,5-bis(trifluoromethyl)phenyl)-3a,4,5,6-tetrahydro-3H-cyclopenta[c]isoxazol-6-yl)-6-(trifluoromethyl)pyridin-3-yl)-4'-methoxy-2-methyl-[1,1'-biphenyl]-4-carboxylic acid 2B. $^1$H NMR (400 MHz, DMSO-d$_6$): δ 8.61 (s, 1H), 8.13 (s, 1H), 7.96 (s, 1H), 7.87-7.85 (m, 2H), 7.80 (t, J=8.00 Hz, 1H), 7.55-7051.00 (m, 1H), 7.40-7.36 (m, 2H), 7.28 (d, J=8.00 Hz, 1H), 7.26 (s, 1H), 6.05 (d, J=8.00 Hz, 1H), 4.53-4.43 (m, 1H), 4.13-4.11 (m, 1H), 3.78 (s, 3H), 2.71-2.65 (m, 1H), 2.36 (s, 3H), 2.15-2.11 (m, 1H), 1.87-1.80 (m, 1H), 1.01-0.97 (m, 1H). MS ESI/APCI calc'd. for $C_{35}H_{25}F_9N_2O_4$ [M+H]$^+$ 709.2, found 709.2. IC$_{50}$ RTA (95% HS): 10,000 nM.

Example 2A

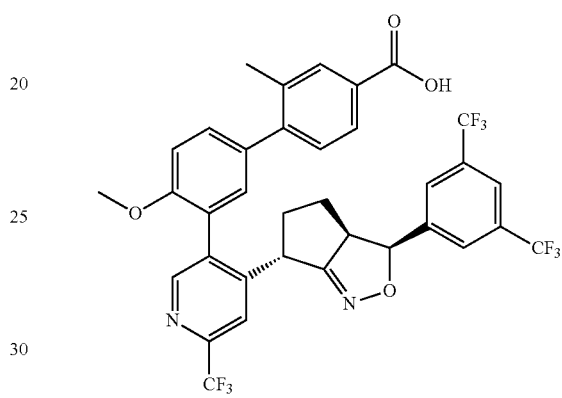

3'-(4-((3S,3aR,6S)-3-(3,5-bis(trifluoromethyl)phenyl)-3a,4,5,6-tetrahydro-3H-cyclopenta[c]isoxazol-6-yl)-6-(trifluoromethyl)pyridin-3-yl)-4'-methoxy-2-methyl-[1,1'-biphenyl]-4-carboxylic acid This compound was synthesized according to the same procedure as was used for Example 2B. MS ESI/APCI calc'd. for $C_{35}H_{25}F_9N_2O_4$ [M+H]$^+$ 709.2, found 709.2. IC$_{50}$ RTA (95% HS): 1,590 nM.

The following compounds in Table 2 were prepared according to general scheme 1 using the procedure outlined in example 1, utilizing commercially available or known halide or boronic acids/esters.

| Examples | Structure | IUPAC Name | Exact Mass [M + H]$^+$ | IC50 (nM) RTA with 95% HS |
|---|---|---|---|---|
| 3 | 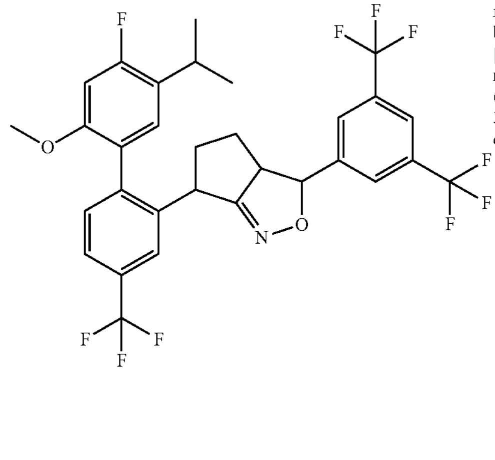 [SMILES: COc1cc(F)c(C(C)C)cc1-c1ccc(C(F)(F)F)cc1C1CCC2C1=NOC2c1cc(C(F)(F)F)cc(C(F)(F)F)c1] | racemic 3-[3,5-bis(trifluoromethyl)phenyl]-6-[4'-fluoro-2'-methoxy-5'-(1-methylethyl)-4-(trifluoromethyl)biphenyl-2-yl]-3a,4,5,6-tetrahydro-3H-cyclopenta[c]isoxazole | Calc'd 634.2, found | 515 |

-continued

| Examples | Structure | IUPAC Name | Exact Mass [M + H]+ | IC50 (nM) RTA with 95% HS |
|---|---|---|---|---|
| 4 | 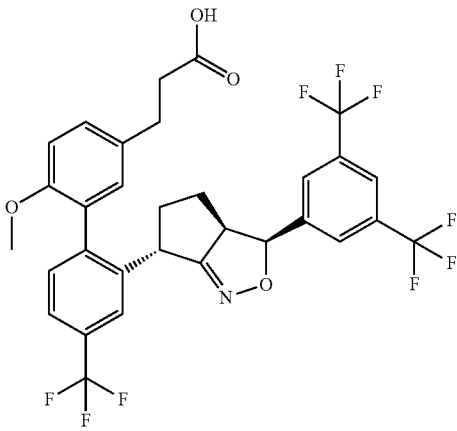 [SMILES: COc1ccc(CCC(=O)O)cc1-c1ccc(C(F)(F)F)cc1[C@@H]1CC[C@@H]2C1=NO[C@@H]2c1cc(C(F)(F)F)cc(C(F)(F)F)c1] | 3-[2'-{(3S,3aR,6S)-3-[3,5-bis(trifluoromethyl)phenyl]-3a,4,5,6-tetrahydro-3H-cyclopenta[c]isoxazol-6-yl}-6-methoxy-4'-(trifluoromethyl)biphenyl-3-yl]propanoic acid | Calc'd 646.2, found | 3.790 |
| 5 | 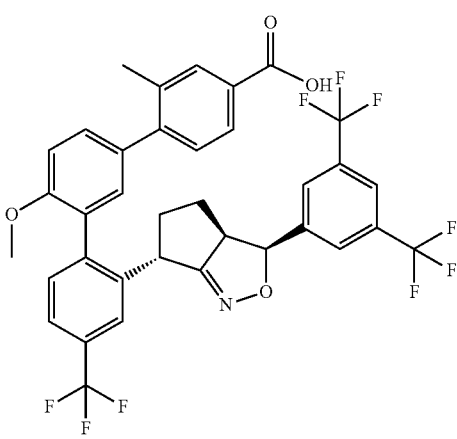 [SMILES: COc1ccc(-c2ccc(C(=O)O)cc2C)cc1-c1ccc(C(F)(F)F)cc1[C@@H]1CC[C@@H]2C1=NO[C@@H]2c1cc(C(F)(F)F)cc(C(F)(F)F)c1] | 2''-{(3S,3aR,6S)-3-[3,5-bis(trifluoromethyl)phenyl]-3a,4,5,6-tetrahydro-3H-cyclopenta[c]isoxazol-6-yl}-4'-methoxy-2-methyl-4''-(trifluoromethyl)-1,1':3',1''-terphenyl-4-carboxylic acid | Calc'd 708.2, found | 145 |
| 6 | 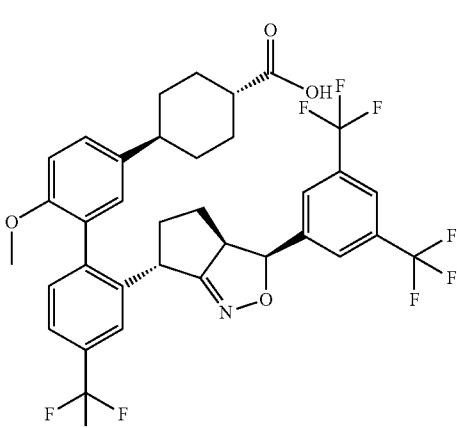 | trans-4-[2'-{(3S,3aR,6S)-3-[3,5-bis(trifluoromethyl)phenyl]-3a,4,5,6-tetrahydro-3H-cyclopenta[c]isoxazol-6-yl}-6-methoxy-4'-(trifluoromethyl)biphenyl-3-yl]cyclohexanecarboxylic acid | Calc'd 700.2, found | 383 |

-continued

| Examples | Structure | IUPAC Name | Exact Mass [M + H]+ | IC50 (nM) RTA with 95% HS |
|---|---|---|---|---|
| 7 | 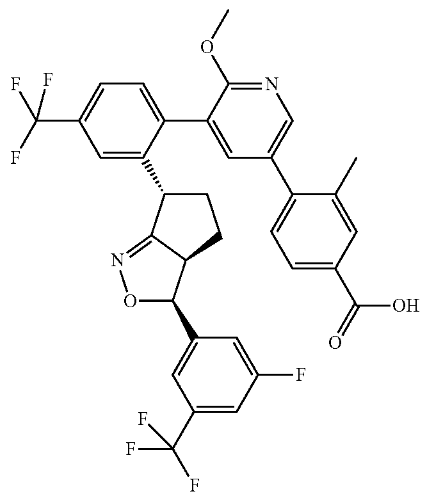 [SMILES: COc1ncc(-c2ccc(C(=O)O)cc2C)cc1-c1ccc(C(F)(F)F)cc1[C@@H]1CC[C@@H]2C1=NO[C@@H]2c1cc(F)cc(C(F)(F)F)c1] | 4-(5-(2-((3S,3aR,6S)-3-(3-fluoro-5-(trifluoromethyl)phenyl)-3a,4,5,6-tetrahydro-3H-cyclopenta[c]isoxazol-6-yl)-4-(trifluoromethyl)phenyl)-6-methoxypyridin-3-yl)-3-methylbenzoic acid | Calc'd 659.2, found 659.2 | 57 |
| 8 | 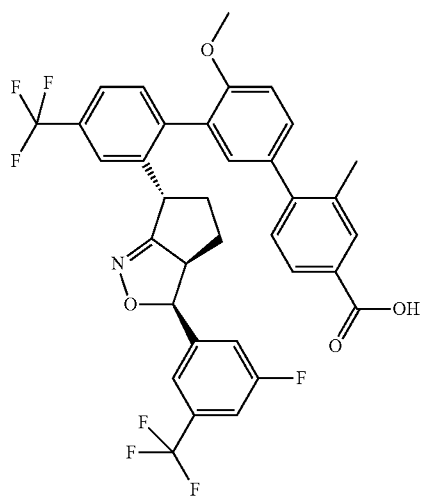 [SMILES: COc1ccc(-c2ccc(C(=O)O)cc2C)cc1-c1ccc(C(F)(F)F)cc1[C@@H]1CC[C@@H]2C1=NO[C@@H]2c1cc(F)cc(C(F)(F)F)c1] | 2''-((3S,3aR,6S)-3-(3-fluoro-5-(trifluoromethyl)phenyl)-3a,4,5,6-tetrahydro-3H-cyclopenta[c]isoxazol-6-yl)-4'-methoxy-2-methyl-4''-(trifluoromethyl)-[1,1':3',1''-terphenyl]-4-carboxylic acid | [M − H]− Calc'd, 656.2, found 656.0 | 36 |
| 9 | 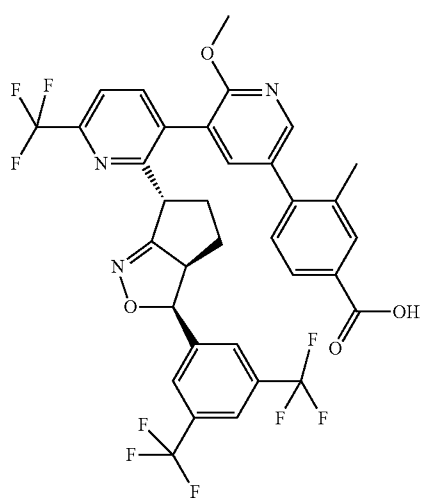 [SMILES: COc1ncc(-c2ccc(C(=O)O)cc2C)cc1-c1ccc(C(F)(F)F)nc1[C@@H]1CC[C@@H]2C1=NO[C@@H]2c1cc(C(F)(F)F)cc(C(F)(F)F)c1] | 4-[2'-{3-[3,5-bis(trifluoromethyl)phenyl]-3a,4,5,6-tetrahydro-3H-cyclopenta[c]isoxazol-6-yl}-2 methoxy-6'-(trifluoromethyl)-3,3'-bipyridin-5-yl]-3-methylbenzoic acid | Calc'd 710.2, found 710.2 | 287 |

| Examples | Structure | IUPAC Name | Exact Mass [M + H]⁺ | IC50 (nM) RTA with 95% HS |
|---|---|---|---|---|
| 10 | 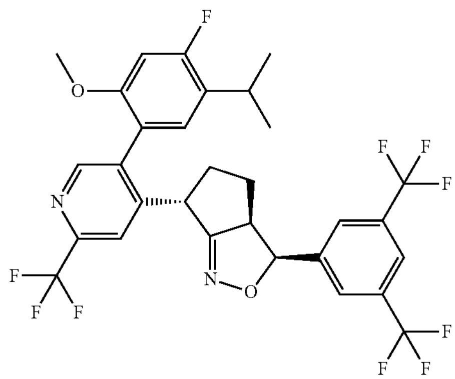 [SMILES: COc1cc(F)c(C(C)C)cc1-c1cnc(C(F)(F)F)cc1[C@@H]1CC[C@@H]2C1=NO[C@@H]2c1cc(C(F)(F)F)cc(C(F)(F)F)c1] | (3S,3aR,6S)-3-(3,5-bis(trifluoromethyl)phenyl)-6-(5-(4-fluoro-5-isopropyl-2-methoxyphenyl)-2-(trifluoromethyl)pyridin-4-yl)-3a,4,5,6-tetrahydro-3H-cyclopenta[c]isoxazole | Calc'd 635.2, found 635.2 | |
| 11 | 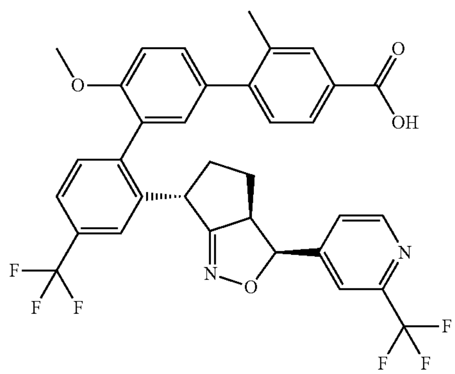 [SMILES: COc1ccc(-c2ccc(C(=O)O)cc2C)cc1-c1ccc(C(F)(F)F)cc1[C@@H]1CC[C@@H]2C1=NO[C@@H]2c1ccnc(C(F)(F)F)c1] | 4'-methoxy-2-methyl-4''-(trifluoromethyl)-2''-((3S,3aR,6S)-3-(2-(trifluoromethyl)pyridin-4-yl)-3a,4,5,6-tetrahydro-3H-cyclopenta[c]isoxazol-6-yl)-[1,1':3',1''-terphenyl]-4-carboxylic acid | Calc'd 641.2, found | |
| 12A | 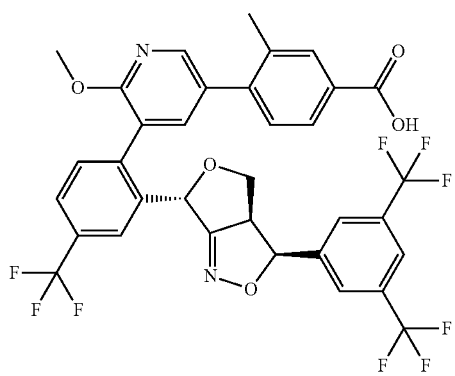 [SMILES: COc1ccc(-c2ccc(C(=O)O)cc2C)cc1-c1ccc(C(F)(F)F)cc1[C@@H]1OC[C@@H]2C1=NO[C@@H]2c1cc(C(F)(F)F)cc(C(F)(F)F)c1] | 4-{5-[2-{3-[3,5-bis(trifluoromethyl)phenyl]-3a,4-dihydro-3H,6H-furo[3,4-c]isoxazol-6-yl}-4-(trifluoromethyl)phenyl]-6-methoxypyridin-3-yl}-3-methylbenzoic acid | Calc'd 711.2, found | |
| 12B | 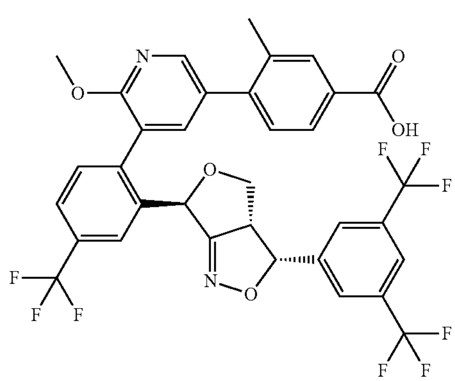 [SMILES: COc1ccc(-c2ccc(C(=O)O)cc2C)cc1-c1ccc(C(F)(F)F)cc1[C@H]1OC[C@H]2C1=NO[C@H]2c1cc(C(F)(F)F)cc(C(F)(F)F)c1] | 4-{5-[2-{3-[3,5-bis(trifluoromethyl)phenyl]-3a,4-dihydro-3H,6H-furo[3,4-c]isoxazol-6-yl}-4-(trifluoromethyl)phenyl]-6-methoxypyridin-3-yl}-3-methylbenzoic acid | Calc'd 711.2, found | |

| Examples | Structure | IUPAC Name | Exact Mass [M + H]+ | IC50 (nM) RTA with 95% HS |
|---|---|---|---|---|
| 13A | 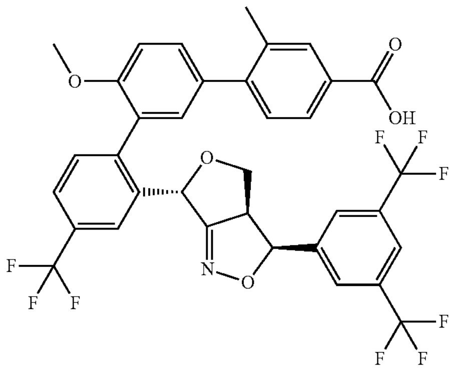 | 2"-{3-[3,5-bis(trifluoromethyl)phenyl]-3a,4-dihydro-3H,6H-furo[3,4-c]isoxazol-6-yl}-4'-methoxy-2-methyl-4"-(trifluoromethyl)-1,1':3',1"-terphenyl-4-carboxylic acid | Calc'd 710.2, found | |
| 13B | 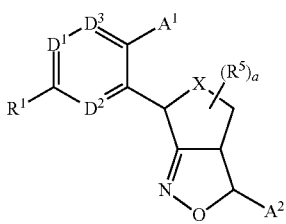 | 2"-{3-[3,5-bis(trifluoromethyl)phenyl]-3a,4-dihydro-3H,6H-furo[3,4-c]isoxazol-6-yl}-4'-methoxy-2-methyl-4"-(trifluoromethyl)-1,1':3,1"-terphenyl-4-carboxylic acid | Calc'd 710.2, found | |

What is claimed is:
1. A compound of Formula I, or a pharmaceutically acceptable salt thereof:

I wherein X is —$CH_2$—, —O—, —C(=O)—, S, —S(O)—, —S(O)$_2$—, —C(=NR)—, or —NR—;
R is H, —CN, or —$C_1$-$C_5$ alkyl;
$R^1$ is H, —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —$NR^6R^7$, —$CO_2R^8$, —C(O)$NR^6R^7$, —$SO_2NR^6R^7$, HET(3), or $C_{3-6}$ cycloalkyl optionally having 1-2 double bonds, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, and —$OC_2$-$C_5$ alkynyl are each optionally substituted with 1-7 halogens, and wherein HET(3) and $C_{3-6}$ cycloalkyl optionally having 1-2 double bonds are optionally substituted with 1-3 substituent groups which are each independently halogen, —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, or —$OC_2$-$C_3$ alkynyl, wherein —$C_1$-$C_3$ alkyl, —$OC_1$-$C_3$ alkyl, —$C_2$-$C_3$ alkenyl, —$OC_2$-$C_3$ alkenyl, —$C_2$-$C_3$alkynyl, and —$OC_2$-$C_3$ alkynyl are each optionally substituted with 1-7 halogens;
$R^6$ and $R^7$ are each independently H, —$C_1$-$C_5$ alkyl, phenyl, naphthyl, $C_{3-6}$ cycloalkyl optionally having 1-2 double bonds, or HET(3), wherein when $R^6$ and $R^7$ are each alkyl, $R^6$ and $R^7$ are optionally joined to form a 4-7 membered cyclic amine group which is optionally substituted with 1-2 groups independently selected from halogen, $CH_3$, $CF_3$, $OCH_3$, or $OCF_3$, wherein phenyl, naphthyl, $C_{3-6}$ cycloalkyl, and HET(3) are optionally substituted with 1-3 substituent groups which are each independently halogen, —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, or —$OC_2$-$C_3$ alkynyl, wherein —$C_1$-$C_3$ alkyl, —$OC_1$-$C_3$ alkyl, —$C_2$-$C_3$ alkenyl, —$OC_2$-$C_3$ alkenyl, —$C_2$-$C_3$alkynyl, and —$OC_2$-$C_3$ alkynyl are each optionally substituted with 1-7 halogens;
$R^8$ is H or —$C_{1-5}$alkyl optionally substituted with 1-7 halogens;
HET(3) is a 3-6 membered heterocyclic ring having 1-3 heteroatom groups which are each independently N, NH, O, S, S(O), or S(O)$_2$ and optionally having 1-3 double bonds;
$D^1$ is N or $CR^2$;
$D^2$ is N or $CR^3$;
$D^3$ is N or $CR^4$;
$R^2$, $R^3$, and $R^4$ are each independently H, —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —NR$^6$R$^7$, —CO$_2$R$^8$, —C(O)NR$^6$R$^7$, or —SO$_2$NR$^6$R$^7$, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, and —OC$_2$-C$_5$ alkynyl are optionally substituted with 1-7 halogens;

Each R$^5$ is independently —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, —OC$_2$-C$_5$ alkynyl, —OH, halogen, —CN, —NR$^6$R$^7$, —CO$_2$R$^8$, —C(O)NR$^6$R$^7$, or —SO$_2$NR$^6$R$^7$, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, and —OC$_2$-C$_5$ alkynyl are optionally substituted with 1-7 halogens;

A$^1$ is phenyl, HET(1), or C$_3$-C$_8$ cycloalkyl optionally having 1-2 double bonds, wherein A$^1$ is optionally substituted with one substituent group Z and is optionally substituted with 1-3 groups which are each independently —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, —OC$_2$-C$_5$ alkynyl, halogen, —OH, or —CN, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, and —OC$_2$-C$_5$ alkynyl are optionally substituted with 1-7 halogens;

HET(1) is a 5- or 6-membered heterocyclic ring having 1-4 heteroatom groups which are each independently —N—, —NH—, —S—, —O—, —S(O)—, or —S(O)$_2$—, optionally having one group —C(=O)—, and optionally having 1-3 double bonds;

Z is A$^3$, —C$_1$-C$_3$ alkylene-CO$_2$R$^8$, —C$_1$-C$_3$ alkylene-C(O)NR$^6$R$^7$, —C$_1$-C$_3$ alkylene-SO$_2$NR$^6$R$^7$, —CO$_2$R$^8$, —C(O)NR$^6$R$^7$, —SO$_2$NR$^6$R$^7$, or —C$_1$-C$_3$alkylene-HET(2), wherein —C$_1$-C$_3$alkylene in all uses is optionally substituted with 1-6 halogens, 1-2 CH$_3$, and 1 —OH, and HET(2) is optionally substituted with 1-3 substituents which are independently —C$_{1-3}$alkyl optionally substituted with 1-5 halogens, —OC$_{1-3}$ alkyl optionally substituted with 1-5 halogens, halogen or NR$_6$R$_7$;

A$^3$ is phenyl, C$_3$-C$_6$ cycloalkyl optionally having 1-2 double bonds, or HET(1), wherein A$^3$ is optionally substituted with 1-3 groups which are each independently —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, —OC$_2$-C$_5$ alkynyl, halogen, —OH, or —CN, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$ alkynyl, and —OC$_2$-C$_5$ alkynyl are optionally substituted with 1-7 halogens; and A$^3$ is optionally substituted with one group which is HET(2), —C$_{1-4}$ alkylene-CO$_2$R$^8$, —C$_{1-4}$alkylene-C(O)NR$^6$R$^7$, —C$_1$-C$_4$alkylene-SO$_2$NR$^6$R$^7$, —CO$_2$R$^8$, —C(O)NR$^6$R$^7$, —SO$_2$NR$^6$R$^7$, or —C(O)NR$^6$C$_{3-6}$cycloalkyl in which C$_{3-6}$cycloalkyl is optionally substituted with 1-3 substituents which are independently selected from halogen, C$_{1-2}$alkyl, and —CN, wherein —C$_1$-C$_4$alkylene in all uses is optionally substituted with 1-7 halogens; and wherein HET(2) is optionally substituted with 1-3 groups which are each independently halogen, —C$_{1-5}$alkyl optionally substituted with 1-7 halogens, —OC$_{1-5}$alkyl optionally substituted with 1-7 halogens, or NR$^6$R$^7$;

HET(2) is a 5-6 membered heterocyclic ring having 1-3 heteroatom groups which are each independently N, NH, O, or S, optionally having one group —C(=O)—, and optionally having 1-3 double bonds;

A$^2$ is phenyl or HET(1), wherein A$^2$ is optionally substituted with 1-3 substituent groups which are each independently —C$_1$-C$_5$ alkyl, —OC$_1$-C$_5$ alkyl, —C$_2$-C$_5$ alkenyl, —OC$_2$-C$_5$ alkenyl, —C$_2$-C$_5$alkynyl, —OC$_2$-C$_5$alkynyl, halogen, —CN, —OH, or C$_{3-6}$cycloalkyl, wherein —C$_1$-C$_5$ alkyl, —OC$_1$-C$_5$ alkyl, —C$_2$-C$_5$ alkenyl, —OC$_2$-C$_5$ alkenyl, —C$_2$-C$_5$alkynyl, and —OC$_2$-C$_5$ alkynyl are optionally substituted with 1-7 halogens, and C$_{3-6}$cycloalkyl is optionally substituted with 1-3 substituents which are each independently halogen, —C$_1$-C$_3$ alkyl, or —OC$_1$-C$_3$ alkyl, wherein-C$_1$-C$_3$ alkyl and —OC$_1$-C$_3$ alkyl are each optionally substituted with 1-7 halogens; and a is 0 or an integer from 1-6.

2. The compound of claim 1, or a pharmaceutically acceptable salt thereof:

wherein R$^1$ is —C$_1$-C$_5$ alkyl, —OC$_1$-C$_5$ alkyl, halogen, —NR$^6$R$^7$, HET(3), or C$_{3-6}$ cycloalkyl optionally having 1-2 double bonds, wherein —C$_1$-C$_5$ alkyl and —OC$_1$-C$_5$ alkyl are optionally substituted with 1-7 halogens, and wherein HET(3) and C$_{3-6}$ cycloalkyl optionally having 1-2 double bonds are optionally substituted with 1-3 substituent groups which are each independently halogen, CH$_3$, CF$_3$, OCH$_3$, or OCF$_3$;

At least one of D$^1$, D$^2$, and D$^3$ is CR$^2$, CR$^3$, or CR$^4$;

R$^2$, R$^3$, and R$^4$ are each independently H, —C$_1$-C$_5$ alkyl, —OC$_1$-C$_5$ alkyl, or halogen, wherein —C$_1$-C$_5$ alkyl and —OC$_1$-C$_5$ alkyl are optionally substituted with 1-7 halogens;

Each R$^5$ is independently —C$_1$-C$_5$ alkyl, —OC$_1$-C$_5$ alkyl, or halogen, wherein —C$_1$-C$_5$ alkyl and —OC$_1$-C$_5$ alkyl are optionally substituted with 1-7 halogens;

A$^1$ is phenyl, HET(1), or C$_3$-C$_6$ cycloalkyl optionally having 1-2 double bonds, wherein A$^1$ is optionally substituted with one substituent group Z and is optionally substituted with 1-3 groups which are each independently halogen, —OH, —CN, —C$_{1-5}$alkyl optionally substituted with 1-7 halogens, or —OC$_{1-5}$alkyl optionally substituted with 1-7 halogens;

A$^3$ is phenyl, C$_3$-C$_6$ cycloalkyl optionally having 1-2 double bonds, or HET(1), wherein A$^3$ is optionally substituted with 1-3 groups which are each independently —C$_1$-C$_5$ alkyl optionally substituted with 1-7 halogens, —OC$_1$-C$_5$ alkyl optionally substituted with 1-7 halogens, —OH, or halogen, and is optionally substituted with one group which is HET(2), —C$_{1-2}$alkylene-CO$_2$R$^8$, —C$_{1-2}$alkylene-C(O)NR$^6$R$^7$, —C$_1$-C$_2$alkylene-SO$_2$NR$^6$R$^7$, —CO$_2$R$^8$, —C(O)NR$^6$R$^7$, —SO$_2$NR$^6$R$^7$, or —C(O)NR$^6$C$_{3-6}$cycloalkyl C$_{3-6}$cycloalkyl is optionally substituted with 1-3 substituents which are independently selected from halogen, C$_{1-2}$alkyl, and —CN, wherein —C$_1$-C$_2$alkylene is optionally substituted with 1-3 halogens; and wherein HET(2) is optionally substituted with 1-3 groups which are each independently halogen, —C$_{1-5}$alkyl optionally substituted with 1-7 halogens, —OC$_{1-5}$alkyl optionally substituted with 1-7 halogens, or NR$^6$R$^7$;

A$^2$ is phenyl or HET(1), wherein A$^2$ is optionally substituted with 1-3 substituent groups which are each independently C$_{1-5}$alkyl optionally substituted with 1-7 halogens, —OC$_{1-5}$alkyl optionally substituted with 1-7 halogens, halogen, —OH, —CN, or C$_{3-6}$cycloalkyl optionally substituted with 1-3 substituents which are each independently halogen, CF$_3$, CH$_3$, —OCF$_3$, or —OCH$_3$; and a is 0 or an integer from 1-3.

3. The compound of claim 2, or a pharmaceutically acceptable salt thereof:

wherein X is —CH$_2$— or —O—;

R$^1$ is CH$_3$, CF$_3$, —OCH$_3$, —OCF$_3$, halogen, or —NR$^6$R$^7$;

R$^6$ and R$^7$ are each independently H or —C$_1$-C$_5$ alkyl;

R², R³, and R⁴ are each independently H, C₁₋₃alkyl, CF₃, —OC₁₋₃alkyl, —OCF₃, or halogen;

Each R⁵ is independently CH₃, CF₃, —OCH₃, —OCF₃, or halogen;

A¹ is phenyl, HET(1), or C₃-C₆ cycloalkyl optionally having 1-2 double bonds, wherein A¹ is optionally substituted with one substituent group Z and is optionally substituted with 1-3 groups which are each independently —C₁₋₃alkyl optionally substituted with 1-5 halogens, —OC₁₋₃ alkyl optionally substituted with 1-5 halogens, halogen, —OH, or —CN;

Each HET(1) is a 5- or 6-membered heterocyclic ring having 1-3 heteroatom groups which are each independently —N—, —NH—, —S—, or —O—, optionally having one group —C(=O)—, and optionally having 1-3 double bonds;

Z is A³, —(CH₂)₁₋₃—CO₂R⁸, —(CH₂)₁₋₃—C(O)NR⁶R⁷, —(CH₂)₁₋₃—SO₂NR⁶R⁷, —CO₂R⁸, —C(O)NR⁶R⁷, —SO₂NR⁶R⁷, or —(CH₂)₁₋₃-HET(2), wherein HET(2) is optionally substituted with 1-3 substituents which are independently —C₁₋₃alkyl optionally substituted with 1-5 halogens, —OC₁₋₃alkyl optionally substituted with 1-5 halogens, halogen or NR⁶R⁷;

R⁸ is H or —C₁₋₃ alkyl optionally substituted with 1-3 halogens;

A³ is phenyl, C₃-C₆ cycloalkyl optionally having 1-2 double bonds, or HET(1), wherein A³ is optionally substituted with 1-3 groups which are each independently CH₃, CF₃, —OCH₃, —OCF₃, —OH, or halogen, and is optionally substituted with one group which is HET(2), —(CH₂)₁₋₂—CO₂R⁸, —(CH₂)₁₋₂—C(O)NR⁶R⁷, —(CH₂)₁₋₂—SO₂NR⁶R⁷, —CO₂R⁸, —C(O)NR⁶R⁷, —SO₂NR⁶R⁷, or —C(O)NR⁶cyclopropyl, wherein cyclopropyl is optionally substituted with 1-3 substituents which are independently selected from 1-3 halogens, one CH₃, and one —CN, and HET(2) is optionally substituted with 1-3 groups which are each independently CH₃, CF₃, —OCH₃, —OCF₃, halogen, or NR⁶R⁷;

A² is phenyl or HET(1), wherein A² is substituted with 1-3 substituent groups which are each independently CH₃, CF₃, —OCH₃, —OCF₃, halogen, —CN, —OH, or C₃₋₄cycloalkyl optionally substituted with 1-3 substituents which are each independently halogen, CF₃, CH₃, —OCF₃, or —OCH₃; and a is 0, 1, or 2.

4. The compound of claim 3, or a pharmaceutically acceptable salt thereof, wherein:

R¹ is CH₃, CF₃, —OCH₃, —OCF₃, F, Cl, or —NR⁶R⁷;
R⁶ and R⁷ are each independently H or —C₁-C₃ alkyl;
D¹ is N or CR², wherein R² is H, —C₁₋₃alkyl, F, or Cl;
D² is N or CR³, wherein R³ is H, —C₁₋₃alkyl, F, or Cl;
D³ is N or CR⁴, wherein R⁴ is H, —C₁₋₃alkyl, F, or Cl;
At least one of D¹, D², or D³ is CR², CR³, or CR⁴;
R⁵ is H or CH₃;
A¹ is phenyl, pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, cyclopropyl, cyclobutyl, cyclohexyl, cyclohexenyl, cyclopentyl, or cyclopentenyl, wherein A¹ is optionally substituted with 1-3 groups which are each independently F, Cl, —OCH₃, —OCF₃, —C₁₋₃alkyl, —CN, or CF₃, and optionally one substituent group Z;
Z is A³, —CH₂CH₂CO₂R⁸, —CH₂CH₂C(O)NR⁶R⁷, —CH₂CH₂SO₂NR⁶R⁷, or —CH₂CH₂-HET(2), wherein HET(2) is optionally substituted with 1-2 substituent groups which are each independently CH₃, CF₃, —OCH₃—OCF₃, halogen, or NR⁶R⁷;

R⁸ is H or —CH₃;
HET(2) is a 5-membered heterocyclic ring having 1-3 heteroatom groups which are each independently N, NH, O, or S, optionally having one group —C(=O), and optionally having 1-3 double bonds;
A³ is phenyl, cyclopropyl, cyclobutyl, cyclohexyl, cyclohexenyl, cyclopentyl, cyclopentenyl, or HET(1), wherein HET(1) is pyridinyl, pyrazinyl, pyrimidinyl, pyridazinyl, pyrazolyl, imidazolyl, isoxazolyl, thiazolyl, oxadiazolyl, thiadiazolyl, oxazolyl, pyrrolyl, thienyl, furyl, or a 5-6-membered heterocyclic ring having 1-2 heteroatom groups which are independently —N—, —NH— or —O—, and optionally one —C(=O)— group, wherein A³ is optionally substituted with 1-2 groups which are each independently CH₃, CF₃, —OCH₃, —OCF₃, —OH, or halogen, and is optionally substituted with 1 group which is —CO₂R⁸, —C(O)NR⁶R⁷, —SO₂NR⁶R⁷, HET(2), or —C(O)NR⁶cyclopropyl wherein cyclopropyl is optionally substituted with 1-3 substituents which are independently selected from 1-3 halogens, one CH₃ and one —CN, and HET(2) is optionally substituted with 1-2 substituent groups which are each independently CH₃, CF₃, —OCH₃, —OCF₃, halogen, or NR⁶R⁷;
A² is phenyl or HET(1) wherein A² is optionally substituted with 1-3 substituent groups which are each independently CF₃, CH₃, F, Cl, —CN, or cyclopropyl; and
a is 0 or 1.

5. The compound of claim 4 having Formula 1a, or a pharmaceutically acceptable salt thereof:

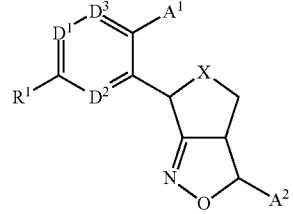

Ia wherein X is —CH₂— or —O—;
R¹ is CF₃, F, or —N(CH₃)₂;
R⁶ and R⁷ are each independently H or —CH₃;
D¹ is N or CR², wherein R² is H or C₁₋₃alkyl;
D² is N or CR³, wherein R³ is H or CH₃;
D³ is N or CR⁴, wherein R⁴ is H or CH₃;
A¹ is phenyl, pyridinyl, thienyl, furyl, cyclohexenyl, or cyclopentenyl, wherein A¹ is optionally substituted with 1-3 groups which are each independently F, Cl, —OCH₃, isopropyl, —CN, —CH₃, or CF₃, and optionally one substituent group Z;
Z is A³, —CH₂CH₂CO₂R⁸, —CH₂CH₂-(5-oxo-4,5-dihydro-1,3,4-oxadiazol-2-yl), or —CH₂CH₂-(5-amino-1,3,4-oxadiazol-2-yl);
R⁸ is H or —CH₃;
A³ is phenyl, cyclobutyl, cyclopentyl, cyclohexyl, or HET(1), wherein HET(1) is pyridinyl, 6-oxopiperidinyl, 2-oxo-1,3-oxazolidinyl, 2-oxo-1,3-oxazinanyl, 5-oxopyrrolidinyl, -(5-oxo-4,5-dihydro-1,3,4-oxadiazol-2-yl), or -(5-amino-1,3,4-oxadiazol-2-yl) wherein A³ is optionally substituted with 1-2 groups —CH₃, —OCH₃, or —OH, and is optionally substituted with 1 group which is —CO₂R⁸ or —C(=O)NHcyclopropyl which is optionally substituted with 1-3 groups independently selected from one —CN and 1-3 halogens; and A² is phenyl or pyridinyl, wherein A² is optionally substituted with 1 or 2 groups which are each independently CF₃, CH₃, F, or Cl.

6. The compound of claim 5 having Formula 1a, or a pharmaceutically acceptable salt thereof, wherein R¹ is CF₃;

D¹ is N or CR², wherein R² is H;

D² is N or CR³, wherein R³ is H;

D³ is CR⁴, wherein R⁴ is H;

A¹ is phenyl or pyridinyl, wherein A¹ is optionally substituted with 1-3 groups which are each independently F, —OCH₃, or isopropyl, and optionally one substituent group Z;

Z is A³ or —CH₂CH₂CO₂R⁸;

R⁸ is H or —CH₃;

A³ is phenyl or cyclohexyl, wherein A³ is optionally substituted with 1-2 groups —CH₃ and is optionally substituted with 1 group —CO₂R⁸; and A² is phenyl or pyridinyl, wherein A² is optionally substituted with 1-2 groups which are selected from CF₃ and F.

7. The compound of claim 1, or a pharmaceutically acceptable salt thereof, wherein X is —CH₂—.

8. The compound of claim 1, or a pharmaceutically acceptable salt thereof, wherein X is —O—.

9. The compound of claim 6, or a pharmaceutically acceptable salt thereof, having the structure below:

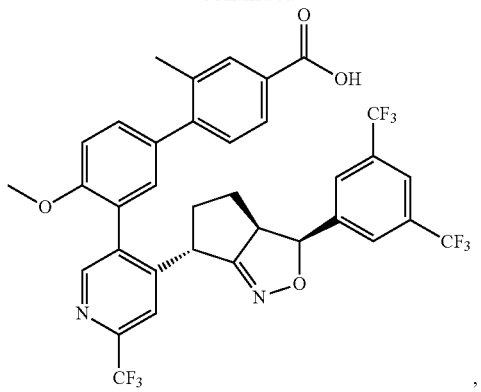

,

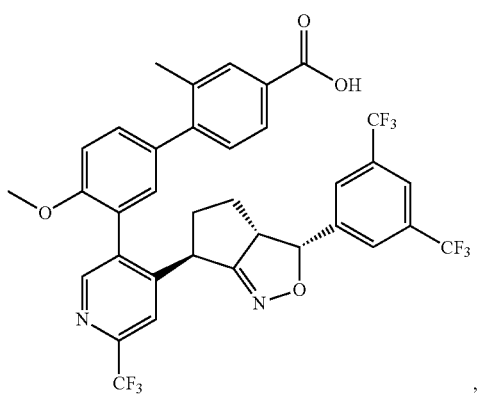

,

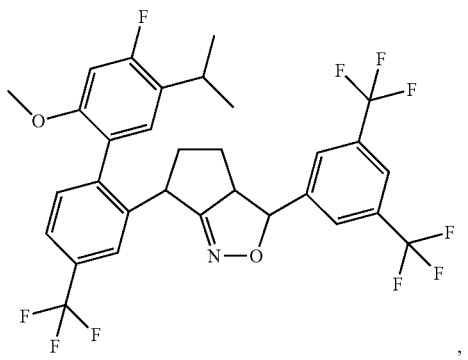

,

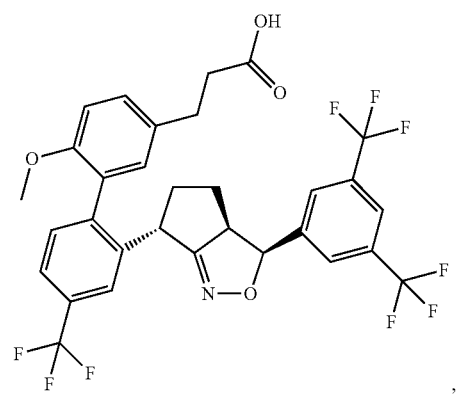

,

55
-continued
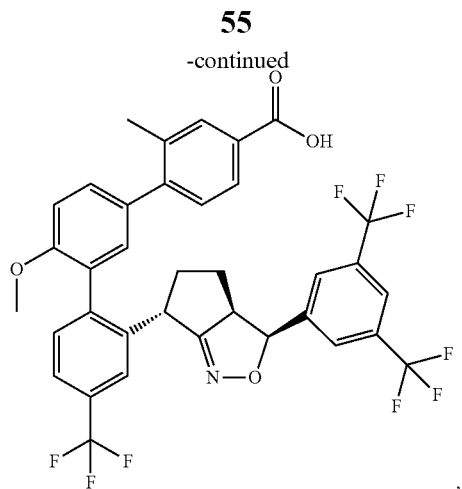
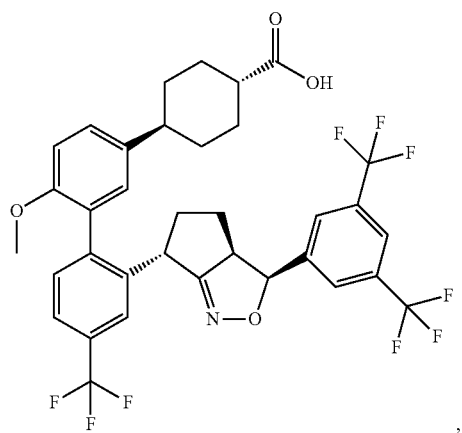
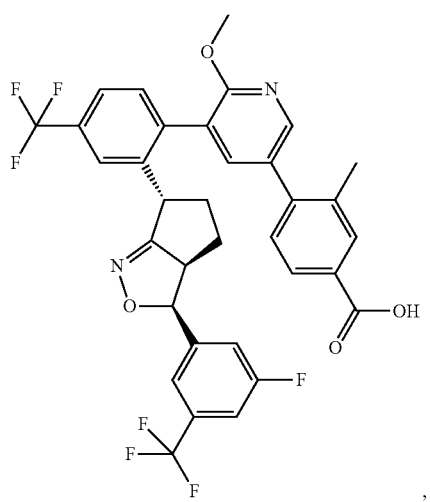
56
-continued
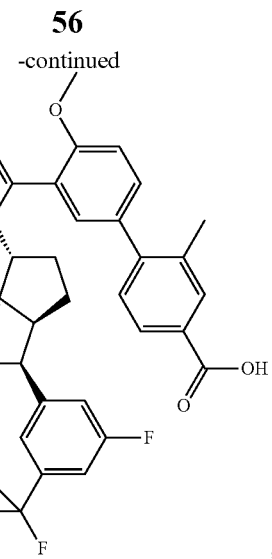
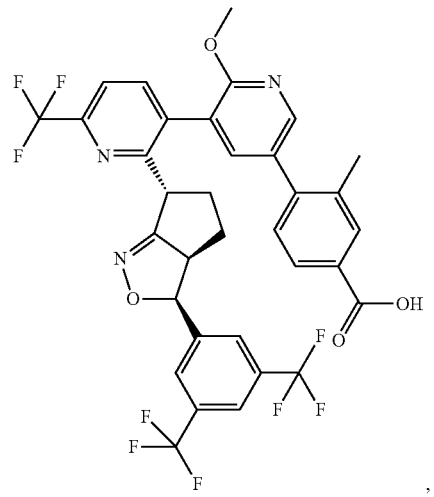
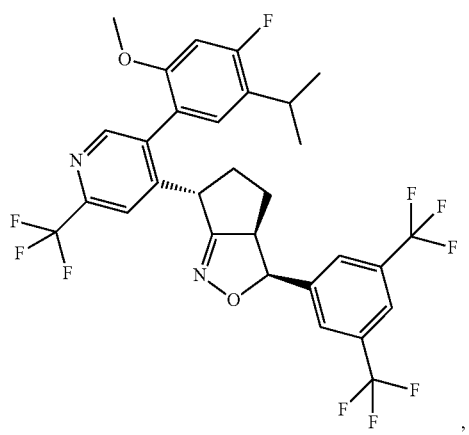

-continued

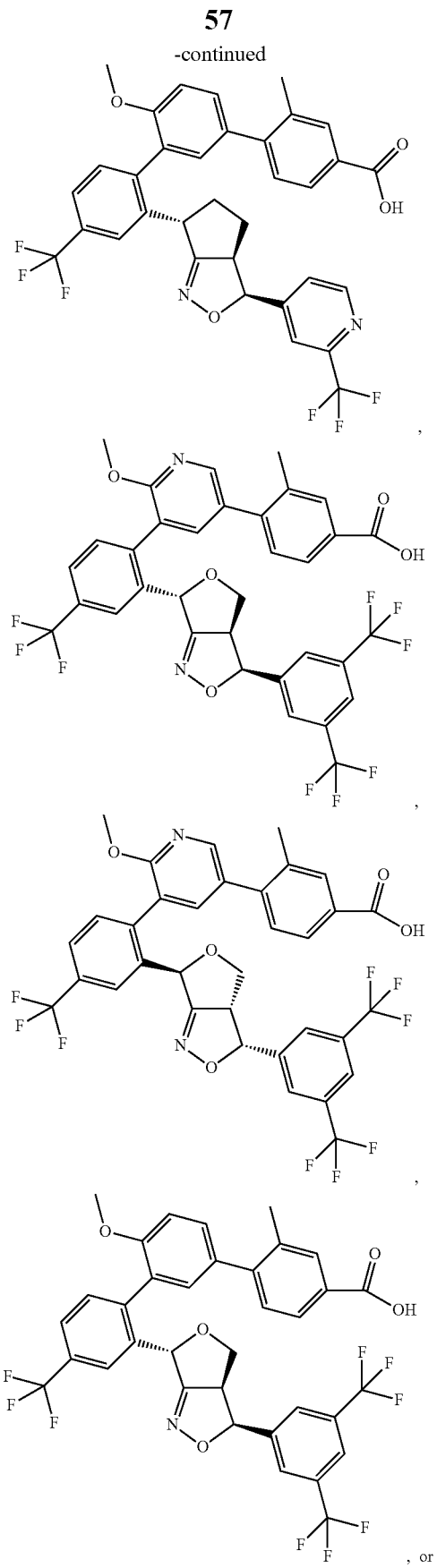

, 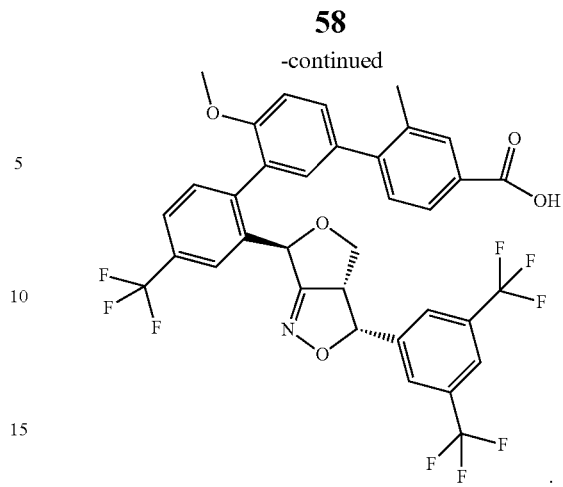

, or

10. A pharmaceutical composition comprising the compound of claim 1 or a pharmaceutically acceptable salt thereof, and a pharmaceutically acceptable carrier.

11. A method of treating atherosclerosis in a patient in need of treatment comprising the administration of a therapeutically effective amount of the compound of claim 1 to said patient, or a pharmaceutically acceptable salt thereof.

12. A method of raising HDL-C in a patient in need of treatment comprising the administration of a therapeutically effective amount of the compound of claim 1 to said patient, or a pharmaceutically acceptable salt thereof.

13. A method of lowering LDL-C in a patient in need of treatment comprising the administration of a therapeutically effective amount of the compound of claim 1 to said patient, or a pharmaceutically acceptable salt thereof.

14. A method of treating dyslipidemia in a patient in need of treatment comprising the administration of a therapeutically effective amount of the compound of claim 1 to said patient, or a pharmaceutically acceptable salt thereof.

15. A pharmaceutical composition comprising the compound of claim 1 or a pharmaceutically acceptable salt thereof, a pharmaceutically acceptable carrier, and one or more active ingredients selected from the group consisting of:
(i) HMG-CoA reductase inhibitors;
(ii) bile acid sequestrants;
(iii) niacin and related compounds;
(iv) PPARα agonists;
(v) cholesterol absorption inhibitors;
(vi) acyl CoA:cholesterol acyltransferase (ACAT) inhibitors;
(vii) phenolic anti-oxidants;
(viii) microsomal triglyceride transfer protein (MTP)/ApoB secretion inhibitors;
(ix) anti-oxidant vitamins;
(x) thyromimetics;
(xi) LDL (low density lipoprotein) receptor inducers;
(xii) platelet aggregation inhibitors;
(xiii) vitamin B12 (also known as cyanocobalamin);
(xiv) folic acid or a pharmaceutically acceptable salt or ester thereof;
(xv) FXR and LXR ligands;
(xvi) agents that enhance ABCA1 gene expression;
(xvii) ileal bile acid transporters; and
(xviii) niacin receptor agonists.

* * * * *